(12) United States Patent
Rodriguez et al.

(10) Patent No.: US 7,749,968 B2
(45) Date of Patent: Jul. 6, 2010

(54) PEPTIDES FOR TARGETING THE PROSTATE SPECIFIC MEMBRANE ANTIGEN

(75) Inventors: Ronald Rodriguez, Glenwood, MD (US); Shawn E. Lupold, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 270 days.

(21) Appl. No.: 10/523,498

(22) PCT Filed: Aug. 5, 2003

(86) PCT No.: PCT/US03/24660

§ 371 (c)(1), (2), (4) Date: Aug. 2, 2006

(87) PCT Pub. No.: WO2006/028429

PCT Pub. Date: Mar. 16, 2006

(65) Prior Publication Data

US 2007/0254316 A1 Nov. 1, 2007

Related U.S. Application Data

(60) Provisional application No. 60/401,151, filed on Aug. 5, 2002, provisional application No. 60/435,140, filed on Dec. 20, 2002.

(51) Int. Cl.
*A61K 38/08* (2006.01)

(52) U.S. Cl. ............................ 514/16; 514/15; 530/328; 530/329

(58) Field of Classification Search ....................... None
See application file for complete search history.

(56) References Cited

U.S. PATENT DOCUMENTS

| 2004/0029197 A1* | 2/2004 | Takimoto et al. | ............ | 435/7.23 |
| 2004/0072753 A1* | 4/2004 | Milton | ........................ | 514/12 |

FOREIGN PATENT DOCUMENTS

WO    WO 00/61605    * 10/2000

OTHER PUBLICATIONS

Terada, et al., FEBS Letters, 1978, 90, 89-92.*
Misawa, 1998, Biochemical and biophysical research communications, 244, 531-539.*
Alfonso, 2000, Journal of Virology, 74(8), 3815-3831.*
Results from the Registry database, Flowpx viru gene FPV221, 2000, 1 page.*
De La Cruz, 1989, The Journal of Immunology, 142, 3568-3575.*

* cited by examiner

*Primary Examiner*—Andrew D Kosar
*Assistant Examiner*—Satyanarayana R Gudibande
(74) *Attorney, Agent, or Firm*—Edwards Angell Palmer & Dodge LLP; Peter F. Corless; Jonathan M. Sparks

(57) ABSTRACT

The invention provides isolated PSMA binding peptides, as well as pharmaceutical compositions thereof. Also provided are diagnostic and therapeutic methods utilizing the PSMA binding peptides, as well as methods for identifying further PSMA binding peptides.

7 Claims, 11 Drawing Sheets

Figure 1. Target Protein: Tag-xPSM

Figure 2: Schematic of Tag-xPSM Phage Display

Figure 9 A.

| Clone | Copies | Sequence |
|---|---|---|
| R5-XC1 | 12 | ---QKHHNYL---- |
| R3-A9 | 1 | ----QRHDYPA--- |
| R4-C10 | 1 | ------HKEQSKM- |
| R4-C18 | 1 | -------DAVRYPV |
| R4-C6 | 1 | LKSHSHQ------- |
| consensus | | ---qkhhnyl---- |

Figure 9 B.

| Clone | Copies | Sequence |
|---|---|---|
| R5-C6 | 12 | ---TITSKRT--- |
| R4-C16 | 1 | ---TPLSPRY--- |
| R5-C2 | 1 | --QTPYDLR---- |
| R3-A4 | 1 | -FPQSSAR----- |
| R3-A6 | 1 | -PPDRSAN----- |
| R4-C8 | 1 | GLPTRTA------ |
| R3-C5 | 1 | ---PIPGLRQ--- |
| R4-C17 | 1 | -KPTNQHK----- |
| R3-A1 | 1 | --PIMLSER---- |
| R5-C10 | 1 | -KPSMMSY----- |
| R3-C8 | 1 | -KPNSQPW----- |
| consensus | | --ptitskrt--- |

Figure 9 C.

| Clone | Copies | Sequence |
|---|---|---|
| R4-C9 | 5 | -----TLVPHTR---- |
| R5-C7 | 1 | ----STRAPHL----- |
| R4-C3 | 1 | --------HTSLKTH |
| R5-C8 | 1 | --------HTKHASH |
| R3-A5 | 1 | ------QFRHSAQ--- |
| R3-A2 | 1 | ------KLQHSST--- |
| R3-C2 | 1 | ------HRLHSTS--- |
| R3-A12 | 1 | ----------HTTTDVY |
| R5-C11 | 1 | ---------PSVNTKQ |
| R4-C1 | 1 | --------KHSVSPS- |
| R5-C9 | 1 | ---SSHSTVH------ |
| R3-A7 | 1 | ----TNSNMHH----- |
| R4-A2 | 1 | ---APNKYKH----- |
| R3-A3 | 1 | -----NKTTHYA---- |
| R5-C3 | 1 | ---SHNDTRH----- |
| R3-C1 | 1 | --LSSNSSL------ |
| R3-C12 | 1 | --TSNNSRI------ |
| R3-A10 | 1 | --SSTNSKL------ |
| R3-C10 | 1 | LTSSVNF-------- |
| R4-C4 | 1 | LSTTISY-------- |
| consensus | | ---s-n-vphtr---- |

SEQUENCE LISTING

<160> NUMBER OF SEQ ID NOS: 111

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Gln Lys His His Asn Tyr Leu Cys
 1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Thr Ile Thr Ser Lys Arg Thr Cys
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Thr Leu Val Pro His Thr Arg Cys
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Ser His Asn Asp Thr Arg His Cys
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Ser Thr Arg Ala Pro His Leu Cys
 1               5

<210> SEQ ID NO 6
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Cys His Thr Lys His Ala Ser His Cys
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Ser Ser His Ser Thr Val His Cys
  1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Lys Pro Ser Met Met Ser Tyr Cys
  1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Pro Ser Val Asn Thr Lys Gln Cys
  1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Gln Thr Pro Tyr Asp Leu Arg Cys
  1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Ala Pro Asn Lys Tyr Lys His Cys
  1               5
```

```
<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Thr Pro Leu Ser Pro Arg Tyr Cys
  1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Asn Lys Ser Ser Leu Gly Thr Cys
  1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys His Thr Ser Leu Lys Thr His Cys
  1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Leu Lys Ser His Ser His Gln Cys
  1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Gly Leu Pro Thr Arg Thr Ala Cys
  1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 17

Cys His Lys Phe Gln Ser Lys Met Cys
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Lys His Ser Val Ser Pro Ser Cys
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Lys Pro Thr Asn Gln His Lys Cys
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Asp Ala Val Arg Tyr Pro Val Cys
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Leu Ser Thr Thr Ile Ser Tyr Cys
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Thr Asn Ser Asn Met His His Cys
 1               5

<210> SEQ ID NO 23
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 23

Cys Gln Phe Arg His Ser Ala Gln Cys
  1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Phe Pro Gln Ser Ser Asp Arg Cys
  1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys His Thr Thr Thr Asp Val Tyr Cys
  1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Pro Ile Met Leu Ser Glu Pro Cys
  1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Thr Ser Asn Asn Ser Ala Ile Cys
  1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Leu Ser Ser Asn Ser Ser Leu Cys
  1               5
```

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Thr Tyr Asn Pro Ser Arg Trp Cys
 1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Leu Ala Ala Pro Thr Gly Lys Cys
 1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Asn Lys Ala Ala Leu Gly Thr Cys
 1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Gly Ser Ala Ala Arg Asn Trp Cys
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Glu Arg Asn Thr Tyr Arg Phe Cys
 1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 34

Cys Lys Ser Gly Glu Val Asn Tyr Cys
  1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Thr Asn Pro Asn Met His His Cys
  1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Pro Gln Pro Ala Ser Arg Gln Cys
  1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Val Ser Pro Asn Leu His Asp Cys
  1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Asn Ala Leu Gln Trp Lys Glu Cys
  1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Asn Thr Gln Pro Pro Arg Thr Cys
  1               5

<210> SEQ ID NO 40
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Leu Asp Gln Asn Tyr Phe Tyr Cys
  1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Asn Leu Leu Tyr Ser Arg Thr Cys
  1               5

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Pro Ala Pro Glu Asn Lys Asn Leu Cys
  1               5                  10

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Pro Lys Gly Met Phe Asn Ser Cys
  1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Leu Gly Met Lys Met Arg Ala Cys
  1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Ser Thr Asn Trp Gln Leu Ser Cys
```

```
<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Ser Glu Trp Thr Trp Asn Asn Cys
 1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Lys Pro Gln Arg Leu Thr Thr Cys
 1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Asn Ala Lys Leu Ser Leu Gln Cys
 1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Leu Ser Ala Ile Asn Arg Val Cys
 1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Ser Leu His Thr Ser Thr Thr Cys
 1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 51

Cys Thr Pro Asp Gly Thr Leu Thr Cys
 1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Gln Pro Asn Leu Arg Pro Met Cys
 1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys His Pro Pro Lys Ser Leu Tyr Cys
 1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Thr Gln Ala His Arg Leu Ile Cys
 1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Pro Lys Thr Met Tyr Leu Gly Cys
 1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Ser Thr Leu Ile His Leu Met Cys
 1               5

<210> SEQ ID NO 57

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Asp Leu His Leu Arg Ser Glu Cys
  1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Cys Thr Pro Glu Asn Thr His Gln Cys
  1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Cys Pro Pro Asn Arg Leu Gln Met Cys
  1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Leu Asn Thr Ala Pro Leu Ala Cys
  1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Lys Leu Arg Thr Gln Met Ala Cys
  1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62
```

```
Cys Leu Asn Pro His Phe Ser Asn Cys
 1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Ser Ser Tyr Ser Leu Gln Val Cys
 1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Gly His Ser Thr Ser Lys Thr Cys
 1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys Ala Pro Lys Leu Arg Phe Asn Cys
 1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Val His Pro His Gly Asn Gln Cys
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Met Gly Leu Asn Thr Gly Arg Cys
 1               5

<210> SEQ ID NO 68
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 68

Cys Ser Asn Val Lys Val Trp Asn Cys
 1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Cys Thr Ala Ala Phe Pro Ala Phe Cys
 1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys His Arg Trp Pro Pro Tyr Ala Cys
 1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Leu Arg Ile Thr Met Gln Thr Cys
 1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Pro Glu Thr Gly Arg Gln Ser Cys
 1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Thr Ser Arg Tyr Asp Asp Gln Cys
 1               5
```

```
<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Cys Pro Pro Trp Ala Ala Pro Tyr Cys
 1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Pro Met Ser Ser Pro Ser Tyr Cys
 1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Cys Ser Arg Leu Tyr Ser Ala Ala Cys
 1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Cys Thr Lys Gly Leu Leu Pro Arg Cys
 1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Leu Met Val Lys Pro Pro Ser Cys
 1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79
```

-continued

```
Cys Leu Thr Glu Ala Ser Arg Leu Cys
  1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Leu Gln Asn Pro Cys Ala Thr Cys
  1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Lys Gln Thr Ser Ala Asn Glu Cys
  1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Cys Asn Thr Pro Leu Ile Lys Val Cys
  1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Ser Pro Val Gly Pro Ala Phe Cys
  1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Arg Thr Thr Ser Asp Ala Leu Cys
  1               5

<210> SEQ ID NO 85
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 85

Cys Ser Leu Asn Thr Arg Ser Gln Cys
  1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Ser Thr His Arg Ala Trp Pro Cys
  1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Ser Glu Ala Leu Asn Pro Ile Cys
  1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Cys Gln Ser Leu Leu Ala Lys Lys Cys
  1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Cys His Phe His His Thr Gly Ala Cys
  1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Cys Asn Pro Ala Ser His Gln Leu Cys
  1               5
```

```
<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Cys Pro Ser Thr Leu Gly Met Thr Cys
  1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Cys Trp His Tyr Pro Ala Asn Asn Cys
  1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Cys Asn Ser Tyr His Thr His His Cys
  1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Cys Gln Arg His Asp Tyr Pro Ala Cys
  1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Cys Phe Pro Gln Ser Ser Ala Arg Cys
  1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 96

Cys Pro Pro Asp Arg Ser Ala Asn Cys
 1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Cys Pro Ile Pro Gly Leu Arg Gln Cys
 1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Cys Pro Ile Met Leu Ser Glu Arg Cys
 1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Cys Lys Pro Asn Ser Gln Pro Trp Cys
 1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Cys Lys Leu Gln His Ser Ser Thr Cys
 1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys His Arg Leu His Ser Thr Ser Cys
 1               5

<210> SEQ ID NO 102
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 102

Cys Asn Lys Thr Thr His Tyr Ala Cys
  1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Cys Thr Ser Asn Asn Ser Arg Ile Cys
  1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Cys Ser Ser Thr Asn Ser Lys Leu Cys
  1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Cys Leu Thr Ser Ser Val Asn Phe Cys
  1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Cys Gln Val Arg His Ser Ala Gln Cys
  1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Cys Thr Pro Gln Ser Ser Asp Arg Cys
  1               5
```

```
<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 108
ccctcatagt tagcgtaacg                                              20

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 109

Gln Lys His His Asn Tyr Leu
  1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 110

Pro Thr Ile Thr Ser Lys Arg Thr
  1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Variable amino acid

<400> SEQUENCE: 111

Ser Xaa Asn Xaa Val Pro His Thr Arg
  1               5
```

PEPTIDES FOR TARGETING THE PROSTATE SPECIFIC MEMBRANE ANTIGEN

RELATED APPLICATIONS

This application claims the benefit of U.S. Provisional Application Ser. No. 60/401,151, filed Aug. 5, 2002, and U.S. Provisional Application Ser. No. 60/435,140, filed Dec. 20, 2002. The entire contents of these applications are incorporated herein by this reference.

GOVERNMENT SUPPORT

This work described herein was supported by a grant from the Department of Defense (Proposal Number PC021004, Award Number DAMD17-03-2-0033, HSRRB Log Number A-11887.3). Therefore, the U.S. Government may have certain rights in the invention.

BACKGROUND OF THE INVENTION

Despite escalating efforts to identify anti-prostate cancer agents, advanced prostate cancer is still a universally progressive and fatal disease. This unusual resistance to conventional chemotherapeutic agents has led to the exploration of a variety of novel therapeutic strategies.

The prostate specific membrane antigen (PSMA) is a type II transmembrane protein found predominantly in the prostate, with minor expression of isoforms in the small intestine, brain, and tumor neovascularity (Heston, W. D (1996) *Urologe A.* 35:400-407). Though the precise function of PSMA is not know, it is known to be a membrane bound carboxypeptidase and folate hydrolase (Heston, W. D (1996) *Urologe A.* 35:400-407). This protein can exist in two forms, PSMA and PSM'. PSMA is the membrane bound form and PSM' is an intracellular form which lacks the transmembrane domain at the amino terminus. PSM' is the predominant form in the benign prostatic cell, while PSMA expression increases and predominates with the more aggressive prostate cancer tumor grades. Importantly, androgen suppression appears to increase PSMA expression in advanced prostate cancers. Hence, this cell surface target has been widely viewed as one of the best cell surface markers for targeted molecular therapeutics. Although there has been theoretical concern that background expression in the intestine and brain may lead to aberrant targeting with this marker, antibody based imaging and therapeutics have failed to demonstrate significant targeting to these ancillary tissues (Yao, D. et al. (2002) *Semin. Urol. Oncol.* 20:211-8). Hence, it appears that from a clinical point of view, PSMA has all the features necessary for consideration as a systemic target for metastatic prostate cancer. Namely, its expression increases in aggressive cancers, androgen suppression results in up regulation and background expression in other tissues does not appear to be a clinically significant source of aberrant targeting (Gong, M. C. et al. (2000) *Mol. Urol.* 4:217-223). Unfortunately, there exist a limited number of methodologies useful for targeting PSMA. Accordingly, there exists a need in the art for additional methods of targeting PSMA for the diagnosis and treatment of prostate cancer.

SUMMARY OF THE INVENTION

The present invention pertains to peptide compounds, pharmaceutical compositions comprising these peptide compounds, and methods of using these peptide compounds. The peptide compounds of the invention bind to the extracellular portion of the human prostate specific membrane antigen (PSMA). Accordingly, the peptide compounds of the invention are useful as modulators of PMSA activity, as well as of modulators of cells which express PMSA (e.g., prostate cancer cells).

In a preferred embodiment, a peptide compound of the invention comprises the amino acid sequence of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, or 107.

In another embodiment, a peptide compound of the invention selectively binds to the extracellular portion of human PSMA and is at least 60%, 65%, 70%, 75%, 80%, 85%, 90%, or 95% identical to the sequence of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, or 107.

In another embodiment, a peptide compound of the invention comprises amino acid residues 2-8 of the peptide sequence of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, or 107.

In another embodiment, the invention provides a polypeptide comprising a peptide compound of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, or 107 and a heterologous peptide. In still another embodiment, the invention provides a peptide compound of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, or 107 and a radioactive moiety and/or a moiety which is toxic to cells.

In another embodiment, the invention provides pharmaceutical compositions comprising a peptide compound of the invention and a pharmaceutically acceptable carrier.

In still another embodiment, the invention provides a method for treating prostate cancer in a subject in of such treatment, comprising administering to the subject a peptide compound of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, or 107. In a further embodiment, the method comprises performing a procedure that removes or destroys prostatic tumor tissue (e.g., radical prostatectomy, cryosurgery, external X-ray therapy, and/or interstitial X-ray therapy). In one embodiment, the peptide compound is administered to the subject prior to performing the procedure that removes or destroys prostatic tumor tissue (e.g., for about 3-6 or 6-12 months prior). In another embodiment, administration of the peptide compound to the subject is continued after performing the procedure that removes or destroys prostatic tumor tissue. In a further embodiment, the method comprises administering to the subject an antiandrogen (e.g., a steroidal antiandrogen and/or a nonsteroidal antiandrogen such as fluamide, bicalutamide, and nilutamide) and/or at least one inhibitor of sex steroid biosynthesis.

In still another embodiment, the invention provides a method for identifying additional PSMA binding peptides comprising varying at least one amino acid residue of a peptide compound selected from the group consisting of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, and 107, and determining the ability of the peptide to bind to PSMA.

Other features and advantages of the invention will be apparent from the following detailed description and claims.

BRIEF DESCRIPTION OF THE DRAWINGS

FIGS. 9A-9C depict the PSMA peptide consensus sequences produced by the alignment of all sequences from phage display rounds 3-5. Clones are named by round (R), background (agarose (A) or cellulose (C)), and clone number. All sequences are depicted without the flanking cysteines. Clone QKHHNYL (i.e., CQKHHNYLC, SEQ ID NO:1) was unique to the cross of the agarose pool selected on cellulase background (XC), while TITSKRT (i.e., CTITSKRTC, SEQ ID NO:2) and TLVPHTR (i.e., CTLVPHTRC, SEQ ID NO:3) were found in both agarose and cellulose backgrounds. The peptide sequences depicted in FIG. 9A are as follows (note: SEQ ID NOs include flanking cysteines not depicted in the alignment): R5-XC1: SEQ ID NO:1; R3-A9: SEQ ID NO:94; R4-C10: SEQ ID NO:17; R4-C18: SEQ ID NO:20; R4-C6: SEQ ID NO:15; consensus: SEQ ID NO:109. The peptide sequences depicted in FIG. 9B are as follows (note: SEQ ID NOs include flanking cysteines not depicted in the alignment): R5-C6: SEQ ID NO:2; R4-C16: SEQ ID NO:12; R5-C2: SEQ ID NO:10; R3-A4: SEQ ID NO:95; R3-A6: SEQ ID NO:96; R4-C8: SEQ ID NO:16; R3-C5: SEQ ID NO:97; R4-C17: SEQ ID NO:19; R3-A1: SEQ ID NO:98; R5-C10: SEQ ID NO:8; R3-C8: SEQ ID NO:99; consensus: SEQ ID NO:110. The peptide sequences depicted in FIG. 9C are as follows (note: SEQ ID NOs include flanking cysteines not depicted in the alignment): R4-C9: SEQ ID NO:3; R5-C7: SEQ ID NO:5; R4-C3: SEQ ID NO:14; R5-C8: SEQ ID NO:6; R3-A5: SEQ ID NO:23; R3-A2: SEQ ID NO:100; R3-C2: SEQ ID NO:10; R3-A12: SEQ ID NO:25; R5-C11: SEQ ID NO:9; R4-C1: SEQ ID NO:18; R5-C9: SEQ ID NO:7; R3-A7: SEQ ID NO:22; R4-A2: SEQ ID NO:11; R3-A3: SEQ ID NO:102; R5-C3: SEQ ID NO:4; R3-C1: SEQ ID NO:28; R3-C12: SEQ ID NO:103; R3-A10: SEQ ID NO:104; R3-C10: SEQ ID NO:105; R4-C4: SEQ ID NO:21; consensus: SEQ ID NO:111.

DETAILED DESCRIPTION OF THE INVENTION

Figure 1:
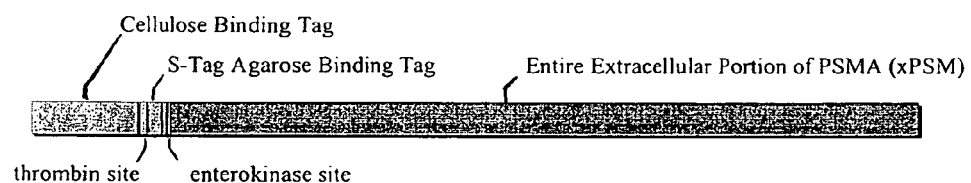
FIG. 1 depicts a schematic of the Tag-xPSM fusion target protein.

The present invention is based, at least in part, on the discovery of peptide compounds capable of binding to the Prostate Specific Membrane Antigen, also referred to interchangeably herein as "PSMA", pharmaceutical compositions comprising the peptide compounds of the invention, and methods of using the peptide compounds to modulate PSMA activity and/or modulate cellular activity of cells expressing PSMA, e.g., prostate cancer cells. For example, the peptide compounds may be used to target diagnostic and/or therapeutic agents to prostate cancer cells.

In a preferred embodiment, the peptides of the invention bind to the extracellular-portion of the Prostate Specific Membrane Antigen (PSMA)(Heston, W. D (1996) Urologe A. 35:400-407). The PSMA protein is a 750 amino acid single-pass transmembrane protein expressed at high levels on the surface of prostate cancer cells. Numerous properties, including alternative splicing, androgen suppression, antibody internalization, and high expression in prostate cancer have made PSMA one of the most promising cell surface targets for prostate cancer. While tools such as antibodies and RNA aptamers exist to bind and target PSMA, there are no reported peptides that bind to PSMA. An advantage of the peptides of the invention described herein is their ability to be genetically transferred to heterologous peptide/polypeptide backgrounds while retaining their ability to bind PSMA. This allows the incorporation of these peptides into multiple therapeutic systems in order to target them to the surface of prostate cancer cells. In addition, the peptides can be synthetically produced for use as targeting agents alone, providing a small peptide targeting system for diagnostic and/or therapeutic agents.

The peptide compounds of the instant invention were identified using phage display technology. A fusion protein consisting of the extracellular portion of PSMA was purified as a target for a random sequence peptide library displayed on an M13 phage coat protein. The phage peptide library was allowed time to bind PSMA fusion protein immobilized to a variety of solid substrates. Weak PSMA binding phage were then washed away and discarded while tight PSMA binder were retained and amplified. This process was repeated several times using both purified PSMA fusion protein and PSMA expression cell lines as targets. Individual phage from PSMA selected pools were isolated and sequenced, identifying multiple potential PSMA binding peptides. The individual phage have the ability to bind PSMA protein, and those tested have the ability to bind PSMA expressing cell lines. All of the identified heptapeptide sequences are flanked by cysteine residues, which are known to form a constrained peptide structure when disulfide bonded. These peptides may be used to bind to PSMA alone or when linked to heterologous peptides or other compounds.

Various aspects of the invention are discussed further in the following subsections. Standard three-letter and one-letter abbreviations for amino acids are used throughout the application.

I. Peptide Compounds

In a preferred embodiment, a peptide compound of the invention comprises an amino acid sequence of any one of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, and 107 (the sequences of which are described in Tables 1a, 1b, 2, 4, 5, and 6). Moreover, longer peptides encompassing these amino acid sequences, as well as peptide derivatives, peptide analogues and peptidomimetics of this amino acid sequence are encompassed by the invention.

The peptides sequences of SEQ ID NOs:1-107 all consist of nine amino acid residues. The first and last amino acid residues of each sequence are cysteine. Without meaning to limit the invention, it is believed that these flanking sequences form a disulfide bond that contributes to the three-dimensional, folded structure of the peptide. Accordingly, the peptide compounds of the invention contain these flanking cysteines. However, it will be appreciated by those of skill in the art that it may be desirable to utilize the peptide compounds of the invention without the flanking cysteines. Accordingly, the peptide compounds of the invention also include any and all peptide sequences comprising amino acid residues 2-8 of SEQ ID NOs:1-107.

In another embodiment, the peptides of the invention may be identified based on a consensus sequence. FIGS. 9A-9C show three alignments of PSMA binding peptides identified by the present invention. As used herein, the consensus sequences do not include the flanking cysteines, which are preferably present, but may not be. It is not necessary that the peptide sequence start at the exact beginning of the consensus. As shown in FIGS. 9A-9C, the peptide sequences may overlap with the consensus at any number of places.

In one embodiment, a peptide of the invention is identified based on the presence Consensus Sequence No. 1 (FIG. 9A), which comprises the sequence Q-K-H-H-N-Y-L (SEQ ID NO:109). In a preferred embodiment, a peptide having Consensus Sequence No. 1 has at least 1, 2, 3, 4, 5, 6, or most preferably, 7 amino acid residues in common with the consensus sequence. In a further preferred embodiment, a peptide having Consensus Sequence No. 1 comprises SEQ ID NO:1, 94, 17, 20, or 15.

In another embodiment, a peptide of the invention is identified based on the presence Consensus Sequence No. 2 (FIG. 9B), which comprises the sequence P-T-I-T-S-K-R-T (SEQ ID NO:110). In a preferred embodiment, a peptide having Consensus Sequence No. 2 has at least 1, 2, 3, 4, 5, 6, or most preferably, 7 amino acid residues in common with the consensus sequence. In a further preferred embodiment, a peptide having Consensus Sequence No. 2 comprises SEQ ID NO:2, 12, 10, 95, 96, 16, 97, 19, 98, 8, or 99.

In still another embodiment, a peptide of the invention is identified based on the presence Consensus Sequence No. 3 (FIG. 9C), which comprises the sequence S-X-N-X-V-P-H-T-R (SEQ ID NO:111), wherein X represents any amino acid residue. In a preferred embodiment, a peptide having Consensus Sequence No. 2 has at least 1, 2, 3, 4, 5, 6, or most preferably, 7 amino acid residues in common with the consensus sequence. In a further preferred embodiment, a peptide having Consensus Sequence No. 3 comprises SEQ ID NO:3, 5, 14, 6, 23, 100, 101, 25, 9, 18, 7, 22, 11, 102, 4, 28, 103, 104, 105, or 21.

As used herein, the terms "peptide", "peptide compound" and "peptidic structure" are intended to include peptides comprised of naturally-occurring L-amino acids, as well as peptide derivatives, peptide analogues and peptide mimetics of the naturally-occurring L-amino acid structures. The terms "peptide analogue", "peptide derivative" and "peptidomimetic" as used herein are intended to include molecules which mimic the chemical structure of a peptide and retain the functional properties of the peptide (e.g., the ability to bind PSMA or a PSMA expressing cell). Approaches to designing peptide analogues, derivatives and mimetics are known in the art. For example, see Farmer, P. S. in Drug Design (E. J. Ariens, ed.) Academic Press, New York, 1980, vol. 10, pp. 119-143; Ball. J. B. and Alewood, P. F. (1990) J. Mol. Recognition 3:55; Morgan, B. A. and Gainor, J. A. (1989) Ann. Rep. Med. Chem. 24:243; and Freidinger, R. M. (1989) Trends Pharmacol. Sci. 10:270.

As used herein, a "derivative" of a compound X (e.g., a peptide or amino acid) refers to a form of X in which one or more reaction groups on the compound have been derivatized with a substituent group. Examples of peptide derivatives include peptides in which an amino acid side chain, the peptide backbone, or the amino- or carboxy-terminus has been derivatized (e.g., peptidic compounds with methylated amide linkages).

As used herein an "analogue" of a compound X (e.g., a peptide or amino acid) refers to a compound which retains chemical structures of X necessary for functional activity of X yet which also contains certain chemical structures which differ from X. An example of an analogue of a naturally-occurring peptide is a peptides which includes one or more non-naturally-occurring amino acids. As used herein, a "mimetic" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) Science 260:1937-1942), peptides in which all L-amino acids are substituted with the corresponding D-amino acids and "retro-inverso" peptides (see U.S. Pat. No. 4,522,752 by Sisto), described further below.

The term mimetic, and in particular, peptidomimetic, is intended to include isosteres. The term "isostere" as used herein is intended to include a chemical structure that can be substituted for a second chemical structure because the steric conformation of the first structure Fits a binding site specific for the second structure. The term specifically includes peptide back-bone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including φ[$CH_2S$], φ[$CH_2NH$], φ[$CSNH_2$], φ[NHCO], φ[$COCH_2$], and φ[(E) or (Z) CH=CH]. In the nomenclature used above, φ indicates the absence of an amide bond. The structure that replaces the amide group is specified within the brackets. Other examples of isosteres include peptides substituted with one or more benzodiazepine molecules (see e.g., James, G. L. et al. (1993) Science 260:1937-1942).

Other possible modifications include an N-alkyl (or aryl) substitution (φ[CONR]), backbone crosslinking to construct lactams and other cyclic structures, substitution of all D-amino acids for all L-amino acids within the compound ("inverso" compounds) or retro-inverso amino acid incorporation (φ[NHCO]). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide. See Goodman et al. "Perspectives in Peptide Chemistry" pp. 283-294 (1981). See also U.S. Pat. No. 4,522,752 by Sisto for further description of "retro-inverso" peptides. Other derivatives include C-terminal hydroxymethyl derivatives, O-modified derivatives (e.g., C-terminal hydroxymethyl benzyl ether) and N-terminally modified derivatives including substituted amides such as alkylamides and hydrazides.

As used herein, the term "amino acid structure" (such as a "leucine structure", a "phenylalanine structure" or a "glutamine structure") is intended to include the amino acid, as well as analogues, derivatives and mimetics of the amino acid that maintain the functional activity of the compound (e.g., the ability to bind PSMA or to PSMA expressing cells). For example, the term "phenylalanine structure" is intended to include phenylalanine as well as pyridylalanine and homophenylalanine. The term "leucine structure" is intended to include leucine, as well as substitution with valine or other natural or non-natural amino acid having an aliphatic side chain, such as norleucine.

The amino- and/or carboxy-terminus of the peptide compounds of the invention can be unmodified hydrogen. Alternatively, the amino- and/or carboxy-terminus of the peptide compound can be modified with a derivative group. Amino-derivative groups which can be present at the N-terminus of a peptide compound include acetyl, aryl, aralkyl, acyl, epoxysuccinyl and cholesteryl groups. Carboxy-derivative groups which can be present at the C-terminus of a peptide compound include alcohol, aldehyde, epoxysuccinate, acid halide, carbonyl, halomethane, and diazomethane groups.

A peptide compound of the invention can comprise additional peptidic structures at the amino and/or carboxy terminus of the core nine amino acid structures.

The peptide compounds of the invention can be prepared by standard peptide synthesis methods known in the art. Non-limiting examples of peptide syntheses are described further in Example 1. The peptide compounds of the invention can also be prepared by preparing nucleic acid molecules that encode the peptides, and expressing the encoded peptides using standard molecular biology methods known in the art. The ability of a peptide compound of the invention to bind to an PSMA or PSMA expressing cells can be evaluated using binding assays. The ability of a peptide compound of the invention to modulate PSMA activity can be evaluated using an assay that measures PSMA activity.

The peptide compounds of the invention may be coupled to other molecules for use in the therapeutic and/or diagnostic methods of the invention. For example, the peptide compounds may be linked other peptides, e.g., carrier peptides, or to molecules which are used for diagnostic and/or therapeutic methods. For example, the peptide compounds of the invention can be used diagnostically to monitor PSMA levels in tissue (e.g., prostate tissue) as part of a clinical testing procedure, e.g., to, for example, determine the efficacy of a given treatment regimen. Detection can be facilitated by coupling (i.e., physically linking) the peptide to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, b-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, $^{32}P$, $^{33}P$, and $^{3}H$.

The peptides of the invention may also be coupled to conjugated to a therapeutic moiety such as a cytotoxin, a therapeutic agent or a radioactive metal ion. A cytotoxin or cytotoxic agent includes any agent that is detrimental and/or toxic to cells. Examples include diphtheria toxin (e.g., diphtheria toxin A), Pseudomonas exdotoxin A, taxol, cytochalasin B, gramicidin D, ethidium bromide, emetine, mitomycin, etoposide, tenoposide, vincristine, vinblastine, colchicine, doxorubicin, daunorubicin, dihydroxy anthracene-dione, mitoxantrone, mithramycin, actinomycin D, dihydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In another embodiment, the invention includes peptides which comprise an amino acid sequence at least about 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to any one of SEQ ID NO:1-107. To determine the percent identity of two amino acid sequences, the sequences are aligned for optimal comparison purposes (e.g., gaps can be introduced in one or both of a first and a second amino acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the peptide sequence of any one of SEQ ID NO:1-107 having 9 amino acid residues, at least 5, preferably at least 6, more preferably at least 7, and even more preferably at least 8 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available online through the website of the Genetics Computer Group), using either a Blosum 62 matrix or a PAM250 matrix, and a gap weight of 16, 14, 12, 10, 8, 6, or 4 and a length weight of 1, 2, 3, 4, 5, or 6.

The invention also provides chimeric or fusion proteins of the peptide compounds described herein. As used herein, a "chimeric protein" or "fusion protein" comprises peptide of the invention operatively linked to heterologous peptide sequences. "Heterologous peptide sequences" includes a peptide or polypeptide having an amino acid sequence corresponding to a protein which is not substantially homologous to peptide compound of the invention. Within the fusion protein, the term "operatively linked" is intended to indicate that the peptide of the invention and the heterologous peptide sequences are fused in-frame to each other. The heterologous peptide sequences can be fused to the N-terminus or C-terminus of the peptide of the invention.

Preferably, a chimeric or fusion protein of the invention is produced by standard recombinant DNA techniques. For example, DNA fragments coding for the different peptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A peptide-encoding nucleic acid can be cloned into such an expression vector such that the fusion moiety is linked in-frame to the peptide.

Peptide compounds of the invention preferably have the ability to selectively bind to the extracellular portion of human PSMA. Accordingly, the invention provides methods for determining whether a peptide compound selectively binds to the extracellular portion of human PSMA. Methods for assaying direct binding of a peptide compound and PSMA are well-known in the art. In a preferred embodiment, a test peptide compound is labeled (e.g., using a radioactive or enzymatic label) and incubated with PSMA (e.g., soluble xPSM or cell-surface PSMA), and the amount of labeled peptide bound to PSMA is determined. In another embodiment, PSMA is labeled, while in still another embodiment, the ability of a peptide compound to bind to PSMA can be determined without the labeling of either interactants, for example, using a technology such as real-time Biomolecular Interaction Analysis (BIA). Sjolander, S, and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules. The peptide compound being tested can be purified peptide or can be operatively linked to a heterologous peptide or phage (as described in the Examples herein).

In another embodiment, the peptide compounds of the invention specifically enhance the enzymatic activity of PSMA. In another embodiment, peptide compounds of the invention may inhibit PSMA activity. Accordingly, the invention provides a method for assaying peptide compounds for the ability to modulate the activity of PSMA. This method is described in detail in Robinson, M. B. et al. (1987) *J. Biol. Chem.* 262:14498-506, incorporated herein by reference, as well as in Example 6 herein. Purified human xPSM (the extracellular portion of human PSMA) is incubated with a radiolabeled substrate, N-acetyl-L-aspartyl-L-[3,4-$^3$H] glutamate, plus the peptide compound being tested. Hydrolyzed substrate is then separated from intact substrate (e.g., by anion exchange chromatography) and quantitated to determine whether the test peptide compound was able to modulate PSMA activity.

II. Pharmaceutical Compositions

Another aspect of the invention pertains to pharmaceutical compositions of the peptide compounds of the invention. The pharmaceutical compositions of the invention typically comprise a peptide compound of the invention and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethelyene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Depending on the route of administration, the compound may be coated in a material to protect it from the action of enzymes, acids and other natural conditions which may inactivate the agent. For example, the compound can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes (Strejan, et al., (1984) J. Neuroimmunol 7:27). Dispersions can also be prepared in glycerol, liquid polyethylene glycols, and mixtures thereof and in oils. Under ordinary conditions of storage and use, these preparations may contain a preservative to prevent the growth of microorganisms.

The active agent in the composition (i.e., a peptide compound of the invention) preferably is formulated in the composition in a therapeutically effective amount. A "therapeutically effective amount" refers to an amount effective, at dosages and for periods of time necessary, to achieve the desired therapeutic result to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

A peptide compound of the invention can be formulated into a pharmaceutical composition wherein the compound is the only active agent therein. Alternatively, the pharmaceutical composition can contain additional active agents. For example, two or more peptide compounds of the invention may be used in combination: Moreover, a peptide compound of the invention can be combined with one or more other agents that have modulatory effects on PSMA activity or on prostate cancer cells.

In another embodiment, the peptide compounds of the invention can be administered to a subject using a viral vector, e.g., an adenoviral vector.

A pharmaceutical composition of the invention, comprising a peptide compound of the invention, can be administered to a subject to modulate PSMA activity in cells of the subject (discussed in further detail below in subsection III). As used herein, the term "subject" is intended to include living organisms in which an PSMA activity occurs, e.g., mammals. Examples of subjects include humans, dogs, cats, mice, rats, and transgenic species thereof.

III. Methods of Treating Prostate Cancer

The methods of the invention generally feature the administration of at least one or more of the peptide compounds of the invention (e.g., a pharmaceutical composition comprising at least one peptide compound of the invention) to a subject (e.g., a male subject) having or at risk of developing prostate cancer, i.e., PSMA-positive prostate cancer. In a preferred embodiment, a peptide compound of the invention is administered in combination with a second therapy, such as performance of a procedure that removes or destroys tumor tissue or administration of an antiandrogen compound.

As used herein, "treatment" of a subject includes the application or administration of a therapeutic agent (e.g., a peptide compound of the invention) to a subject, or application or administration of a therapeutic agent to a cell or tissue from a subject, who has a diseases or disorder (e.g., prostate cancer), has a symptom of a disease or disorder, or is at risk of (or susceptible to) a disease or disorder, with the purpose of curing, healing, alleviating, relieving, altering, remedying, ameliorating, improving, or affecting the disease or disorder, the symptom of the disease or disorder, or the risk of (or susceptibility to) the disease or disorder.

One aspect of the invention pertains to a method for treating prostate cancer in a subject in need of such treatment, comprising administering to the subject a peptide compound of the invention, and performing on the subject at least one procedure that removes or destroys prostatic tumor tissue, such as a radical prostatectomy, cryosurgery, external radiation therapy (e.g., X-ray therapy) or interstitial radiation therapy (e.g., implantation of a radioactive seed). The type, dosage and duration of peptide compound therapy are selected such that efficient binding to PSMA expressing prostate cells is obtained. The peptide compound may be administered to the subject prior to or subsequent to performing the procedure that removes or destroys prostatic tumor tissue. In one such embodiment, administration of a peptide compound is preferably for a period sufficient to cause the prostate or prostatic tumor tissue to shrink in size prior to performing the procedure that removes or destroys prostatic tumor tissue. A suitable period for preadministration of a peptide compound typically is between about one month and about one year, more preferably between about three months and about six months.

In certain situations it may be desirable to use an antiandrogen, and thus in another embodiment, this treatment method can further involve administering an antiandrogen to the subject in combination with the peptide compound. In yet another embodiment, this treatment method can further involve administering one or more inhibitors of sex steroid biosynthesis to the subject in combination with the peptide compound (optionally in further combination with an antiandrogen) prior to or subsequent to performing the procedure that removes or destroys prostatic tumor tissue.

In another embodiment, the peptide compounds of the present invention may be administered in conjunction with an LHRH antagonist, as described in U.S. Pat. Nos. 5,843,902, 5,780,435, and 6,153,586, incorporated herein by reference.

Those of skill in the art will recognize that while it may not be necessary to combine peptide compound therapy with additional drugs or treatments, in certain situations it may be desirable to further combine the peptide compound with other drugs or treatments to achieve the greatest therapeutic effect.

As is discussed in more detail above, a preferred route of administration for a peptide compound is by depot injection or other slow-release or sustained delivery method. A preferred route of antiandrogen administration is oral administration. Radical prostatectomy, cryosurgery or radiation therapy (external or interstitial) can be performed using standard methodologies.

The methods of the present invention can be applied to the treatment of prostate cancer in male subjects at any stage of the cancer, although certain treatment methods are more preferred for particular cancer stages. For reviews on screening and diagnostic methods for prostate cancer, see e.g., Garnick, M. (1993) Annals of Internal Medicine 118:803-818; and Garnick, M. (1994) Scientific American 270:72-81. Prostate cancer is commonly evaluated according to a scale divided into four lettered stages: A, B, C and D. Tumors in stage A are microscopic; stage A1 designates tumors confined to a relatively small area and composed of well-differentiated tissue, while stage $A_2$ tumors are more diffuse and less well differentiated. Stage B tumors are large enough to be felt during a rectal examination, while stage C prostate cancers have spread throughout the gland and typically have pushed past the borders of the prostate into surrounding structures. Stage D tumors have metastasized, e.g., to lymph nodes, bone, or other organs. Alternatively, tumors can be staged by the TNM staging system, in which tumors are ranked on a scale of progressively worsening disease from T1a to T4b (e.g., T1c tumors are non-palpable and non-visible that were detected by elevated blood levels of prostate specific antigen). The methods of the invention are useful in the treatment of any stage of prostate cancer. However, it will be appreciated by the skilled artisan that methods involving procedures for removal or destruction of prostatic tumor tissue preferably are employed with non-metastasized cancers. For example, radical prostatectomy preferably is used with stage A, B and some stage C tumors (i.e., where the tumor growth has not extended considerably beyond the borders of the prostate gland) as well as stage T1c tumors. Radiation therapy (e.g., external or interstitial) preferably is used with stage A, B or C tumors as well as T1c tumors.

To assess the efficacy of a treatment method of the invention, the size of the prostate can be determined by methods known in the art, for example, rectal examination, transrectal ultrasonography or magnetic resonance imaging (MRI). Moreover, the size or extent of the prostate tumor (and metastatic tumors, if any) can be assessed by known methods including a prostate-specific antigen blood test (described further below), bone scanning, X-rays, skeletal survey, intravenous pyelography, CAT-scan, MRI, physical examination, biopsy, and the like. For treatment methods that involve surgery (e.g., in neoadjuvant therapy wherein a peptide compound is administered prior to a radical prostatectomy), the tumor can also be staged during surgery (e.g., the prostate gland can be examined during surgery and/or a biopsy can be taken and examined). Thus, clinical staging and/or surgical staging may be used to evaluate the extent of disease. Use of a peptide compound in accordance with the methods of the invention is expected to result in a tumor stage, assessed at the time of radical prostatectomy, that is improved compared to methodologies that do not include use of a peptide compound of the invention.

A preferred method of evaluating the extent of prostate cancer is to assay the level of prostate-specific antigen (PSA) in a subject's blood. The PSA blood test is a reasonably specific, sensitive, rapid, and inexpensive tool for screening for prostate cancer. In general, a blood PSA level above 4 ng/ml is considered to be suggestive of the presence of prostate cancer, with levels above 10 ng/ml being particularly indicative of cancer. For a subject undergoing treatment with a peptide compound according to the methods of the invention, a pretreatment level of PSA can be established and the efficacy of the treatment assessed by monitoring periodically the PSA level in the subject's blood, wherein decreased PSA levels are used as an indicator of the efficacy of the treatment. The PSA nadir (i.e., the point at which PSA levels do not decrease further even upon further treatment with a peptide compound) can be used as the indicator point for initiation of a second therapy, for example for performance of a procedure that removes or destroys prostatic tumor tissue (such as radical prostatectomy, cryosurgery and/or radiation therapy). It is expected that the PSA nadir will be reached sooner using a peptide compound, as compared to treatments which do not include using a peptide compound.

Additionally or alternatively, plasma concentrations of sex hormones can be monitored to assess the efficacy of the drug therapy. Concentrations of hormones such as testosterone, dihydrotestosterone, dehydroepiandrosterone (DHEA), DHEA-sulfate, androst-5-ene-3β, 17-diol, and the estrogen 17β-estradiol can all be measured by methods known the skilled artisan (see, e.g., F. Labrie et al, (1983) The Prostate 4:579). Preferably, decreased levels of testosterone and dihydrotestosterone are used as indicators of treatment efficacy.

The response criteria for prostate developed by the National Prostate Cancer Project (see e.g., The Prostate, 1:375-382) can also be used to assess the efficacy of treatment. For treatment methods involving a procedure that removes or destroys tumor tissue (such as radical prostatectomy, cryosurgery, and/or radiation therapy), it is preferable to administer a peptide compound until the size of the prostate or a prostate tumor has decreased and/or blood PSA levels have decreased before performing the procedure.

Although the methods of the invention are described in particular with application to the treatment of prostate cancer, it will be appreciated by the skilled artisan that these methods also can be applied to the treatment of other disorders, including cancer, that involve the up- or downregulation of PMSA, in humans or animals of either sex. In such cases, methods involving a step comprising surgical removal of tumor tissue are designed for the removal of the tumor tissue of the particular cancer to be treated.

IV. Modulatory Methods

The peptide compounds of the invention can be used to modulate PSMA activity in a cell expressing the PSMA. A peptide compound of the invention may be an agonist or an antagonist of PSMA activity (which can be evaluated using a functional assay of PSMA activity). Accordingly, the various forms of the term "modulating" as used herein is intended to include "stimulating" PSMA activity and "inhibiting" PSMA activity.

In one embodiment, the invention provides a method of modulating PSMA activity in a cell comprising contacting a cell expressing PSMA (e.g., a prostate cell) with a peptide compound of the invention such that PSMA activity in the cell is modulated.

In one embodiment of the modulatory methods of the invention, the cell expressing PSMA is contacted with the peptide compound in vitro. For example, the peptide compound can be added to the culture medium in which the cells are cultured in vitro. In another embodiment of the modulatory methods of the invention, the peptide compound is administered to a subject such that cell expressing PSMA is contacted with the peptide compound in vivo. Peptide compounds can be administered to a subject as described above in subsection II.

The modulatory methods of the invention may be useful in any of clinical situations that may involve enhanced or diminished PSMA activity. For example, antagonists of PSMA activity may be useful in disease situations in which there is excess PSMA activity and/or expression, e.g., prostate cancer.

V. Diagnostic Methods

The peptide compounds of the invention may be used for detecting the presence or absence of PSMA protein in a biological sample (e.g., a prostate cell sample). In one embodiment, a diagnostic method of the invention involves obtaining a biological sample from a test subject and contacting the biological sample with a peptide compound of the invention that is coupled to a detectable label (as described elsewhere herein) such that the presence of PSMA protein is detected in the biological sample. The term "biological sample" is intended to include tissues, cells and biological fluids isolated from a subject, as well as tissues, cells and fluids present within a subject. In a preferred embodiment, the biological sample is a prostate cell sample. The detection method of the invention can be used to detect PSMA in a biological sample in vitro as well as in vivo.

In another embodiment, the methods further involve obtaining a control biological sample from a control subject, contacting the control sample with a peptide compound of the invention capable of detecting PSMA protein, such that the presence of PSMA protein is detected in the biological sample, and comparing the presence of PSMA protein in the control sample with the presence of PSMA protein in the test sample.

The invention also encompasses kits for detecting the presence of PSMA in a biological sample. For example, the kit can comprise a labeled compound or agent capable of detecting PSMA protein in a biological sample; means for determining the amount of PSMA in the sample; and means for comparing the amount of PSMA in the sample with a standard. The compound or agent can be packaged in a suitable container. The kit can further comprise instructions for using the kit to detect PSMA protein.

VI. Methods of Identifying Higher Affinity PSMA Specific Peptides

The peptides of the present invention may also be used to identify additional peptides with higher binding affinities for PSMA. For example, a peptide library may be constructed by subjecting one or more of the peptides of the invention to random mutagenesis (using standard methods). Such a library may then be screened using, for example, phage display, as described in the Examples herein, or as known in the art. The creation of a library based on peptides already identified as PSMA binding peptides allows the screening of greater numbers of peptides that bind PSMA, leading a greater likelihood of identifying novel peptides with higher binding affinities than those already identified herein. In a preferred embodiment, a library is generated using peptides of the invention that contain amino acid residues specific to Consensus Sequence No. 1, 2, or 3 (as described elsewhere herein; see FIG. 9). When a peptide sequence contains residues common to a consensus sequence, it is likely that such common residues are beneficial for binding to the target (i.e., PSMA). Accordingly, a method for identifying higher affinity binding peptides include keeping constant the residues of a peptide sequence that conform to a consensus sequence, while varying non-conforming residues.

This invention is further illustrated by the following examples which should not be construed as limiting. The contents of all references, patents, and published patent applications cited throughout this application, as well as the figures and the sequence listing, are incorporated herein by reference.

EXAMPLES

Materials and Methods

Unless indicated otherwise, the following materials and methods were used in the subsequent examples.

Materials

The M13 phage display library, containing the insert $CX_7C$ (wherein C represents cysteine, and $X_7$ represents seven random amino acid residues), and ER2738 bacteria were acquired from New England Biolabs (Beverly, Mass.). S-tag agarose beads, CBind cellulose resin, recombinant enterokinase, rEK Capture beads, S-tag-HRP, and S-tag assay components were acquired from Novagen, Inc. (Madison, Wis.). LNCaP and PC-3 cells were obtained from the American Type Culture Collection (ATCC, Rockville, Md.). Ready Plaque Sf-9 cells were obtained from Novagen, Inc. Anti-M13 monoclonal antibody, HRP/anti-M13 monoclonal antibody, Anti-mouse Ig, Fluorescine linked whole antibody from sheep, and ABTS were acquired from Amersham Pharmacia Biotech (Buckinghamshire, England). 7E11-C5 antibody was produced from the media of cultured hybridomas (ATCC).

PSMA Immobilization and Purification

The PSMA fusion proteins, Tag-xPSM and xPSM, and their purification have previously been described in detail (See U.S. Patent Application Publication No. 20020119473; and Lupold, S. E. et al. (2002) *Cancer Res.* 62:4029-4033; incorporated herein by reference). Briefly, Ready Plaque Sf-9 cells were plated as monolayers and infected with recombinant virus at a multiplicity of infection (MOI) of 5 plaque-forming units (PFU) per cell. Infected cell media was harvested 72-80 hours post infection, and recombinant protein levels were quantified by S-tag assay. Prior to purification, S-Protein agarose beads were washed several times in Bind/Wash Buffer (20 mM Tris Tris-HCl pH 7.5, 150 mM NaCl) to remove all EDTA. Fusion protein was bound to S-protein agarose, using a ratio of 1 ml S-protein beads per 500 µg fusion protein, for 12-18 hours at room temperature. CBind cellulose resin was resuspended in $dH_2O$ and incubated with fusion protein at a ratio of 40 µg fusion protein per milligram of resin and allowed to bind for 12-18 hours at room temperature. CBind Resin and S-tag Beads were then washed three times with Bind/Wash Buffer, resuspended in 1 ml aliquots, and quantified by S-tag assay and Bradford Assay. These beads were then stored at 4° C. until use in binding or phage selection experiments. In some cases, purified xPSM was released from S-tag agarose by the addition of 10-20 units of recombinant enterokinase (rEK), per 500 µg fusion protein, at 37° C. for 4-16 hours. Finally, rEK was bound for 10 minutes at room temperature by EKapture Agarose Beads using a ratio of 1:1, microliters of beads to micrograms fusion protein. The resulting protein, xPSM, contains no affinity tags and is over 95% pure by evidence of silver staining (Lupold, S. E. et al. (2002) *Cancer Res.* 62:4029-4033).

Tag-xPSM Phage Display

100 µl of S-protein agarose (2× in RPMI 1640+1% Fetal Bovine Serum (FBS) and 100 µl of CBind Resin (10 mg/ml in RPMI 1640+1% FBS) without fusion protein were used to negatively select the original phage display library. $2 \times 10^{11}$ plaque forming units (PFU) of $1.29 \times 10^9$ different sequence phage were incubated with each aliquot of resin for 1 hr at 37° C., while rotating. The S-tag agarose was pelleted and supernatant saved as the agarose counter-selected pool. The cellulose resin was transferred onto 200 µl of 9:1 dibutyl phthalate:cyclohexane and the resin pelleted through the organic phase. The aqueous supernatant was saved as the cellulose counter-selected pool. Each counter selected pool was then added to tag-xPSM agarose or cellulose resin and incubated for 1 hr at 37° C., while rotating. The tag-xPSM agarose was pelleted and washed three times in RPMI 1640+1% FBS. The agarose pellet was then saved for phage isolation. The Tag-xPSM cellulose was transferred onto 200 µl of 9:1 dibutyl phthalate:cyclohexane and the resin pelleted through the organic phase. The tube was then snap frozen in liquid nitrogen to isolate the resin pellet. Over 75% of Tag-xPSM remained bound to the cellulose resin through these conditions. The resulting phage-bound tag-xPSM agarose and tag-xPSM cellulose were then resuspended in 200 µl of log phase ER2738 cells and phage allowed to infect 1 hour at room temperature. A small aliquot was taken at this time to quantitate the number of phage bound per round of selection. The remaining PSMA bound phage was then amplified, tittered, and applied to the next round of phage display. There was only one counter-selection round, followed by a total of five positive selection rounds, applying between $10^{10}$ to $10^{11}$ PFU per round. The final round of selection included cross-selections, where selected phage pools from one PSMA background where applied to the other. Individual phage were isolated and sequenced from rounds three through five.

Sequencing and Analysis

Individual phage plaques were amplified for 5 hours in ER2738 cells at 37° C. Amplified supernatant was incubated 1:1 with PEG/NaCl buffer (20% PEG 8000, 2.5 M NaCl) for 10 minutes at room temperature. Phage were microfuged 10 minutes at 20,000 g, 4° C. The phage pellet was suspended in 100 µl Iodide buffer (10 mM Tris-HCl, pH 8.0, 1 mM EDTA, 4M NaI). Single stranded DNA (ssDNA) was precipitated with 250 µl of 100% ethanol, pelleted, and washed in 70% ethanol. Each ssDNA pellet was suspended in 30 µl 10 mM Tris, pH 7.4. Each phage was sequenced using the Amersham DYE ET mix, by incubating 6 µl ssDNA, 1 µl of 5 µM-96 pill Sequencing Primer (CCCTCATAGTTAGCGTAACG; SEQ ID NO:108), and 8 µl of DYE ET mix in a 96 well PCR plate and amplified by 30 cycles of 95° C. for 20 seconds, 50° C. for 15 seconds, and 60° C. for 1 minute. Sequencing reaction products were spun through G50-fine Sephadex column plates, prepared on Millipore-multiscreen plates. Products were sequenced and analyzed on the MegaBACE capillary sequencer. All sequences, minus the flanking cysteines, were aligned using the Baylor College of Medicine Clustal W1.8 Global Progressive Alignment (available online) with data presented by Boxshade 3.21 software (available online through the Swiss Institute for Bioinformatics).

Enzyme-Linked Immunosorbent Assay

Target proteins were immobilized on 96 well tissue culture plates by incubation for 1-2 hours at room temperature or overnight at four degrees Celsius. Both phage and protein coated plate were blocked for 30 minutes with RPMI 1640+ 1% Bovine Serum Albumin (BSA) at room temperature. Phage were incubated with target in RPMI 1640+1% BSA for 1 hour at room temperature, wells were washed five times in PBS+0.05% Tween-20, and wells were incubated with 1:5000 HRP/anti-M13 monoclonal antibody (in PBS) for 1 hour. Wells were again washed five times in PBS+0.05% Tween-20, and signal detected by incubation in 1×ABTS Stock Solution (100 mg ABTS in 450 ml of 0.05 M Citric Acid, pH 4.0) and absorbance reading at 410 nm. Samples were performed in triplicate and data represents the average result with standard error of the Mean (SEM). Significance was calculated by two-tailed, two-sample equal variance test.

Cell Binding Analysis

Cell monolayers were washed several times in PBS, and finally incubated five minutes in PBS at 37° C. Cells were knocked free, pelleted, and suspended in RPMI 1640+1% FBS at a concentration of $10^6$ cells per milliliter. $10^8$ PFU from each clone were incubated with 100 µl of cells at 37° C. for 20 minutes while rotating. For competitive inhibition, purified xPSM or BSA were added to the cells along with phage, and a larger concentration of $10^{10}$ PFU was applied. The cells were then centrifuged through 200 µl of 9:1 dibutyl phthalate:cyclohexane, previously described as BRASIL portioning (Giordano, R. J. et al. (2001) *Nat. Med.* 7:1249-1253, incorporated herein by reference). The tube was then snap frozen in liquid nitrogen to isolate the cell pellet. The cell pellets were then resuspended in 200 µl of log phase ER2738 cells and phage allowed to infect 1 hour at room temperature. A small aliquot was taken to determine the number of phage bound by dilution titer.

Example 1

Selection of PSMA Binding Peptides Using Tag-xPSM

This example describes the identification of PSMA binding peptides using an in vitro selection strategy. The target fusion protein, referred to herein as "Tag-xPSM" (FIG. 1), used for selection was described previously (Lupold, S. E. et al. (2002) *Cancer Res.* 62:4029-4033), where it was used to identify nuclease stabilized RNA aptamers that bind the extracellular portion of PSMA with nanomolar affinity. Tag-xPSM contains the entire extracellular portion of PSMA, fused to two removable affinity tags. One affinity tag, the Cellulose Binding Domain (CBD), has high affinity for cellulose, while the second affinity tag, the S-tag, has high affinity for the S-protein. This system can therefore be used to purify and immobilize Tag-xPSM on cellulose resin or S-protein agarose beads as a target for a phage display system.

Figure 2:
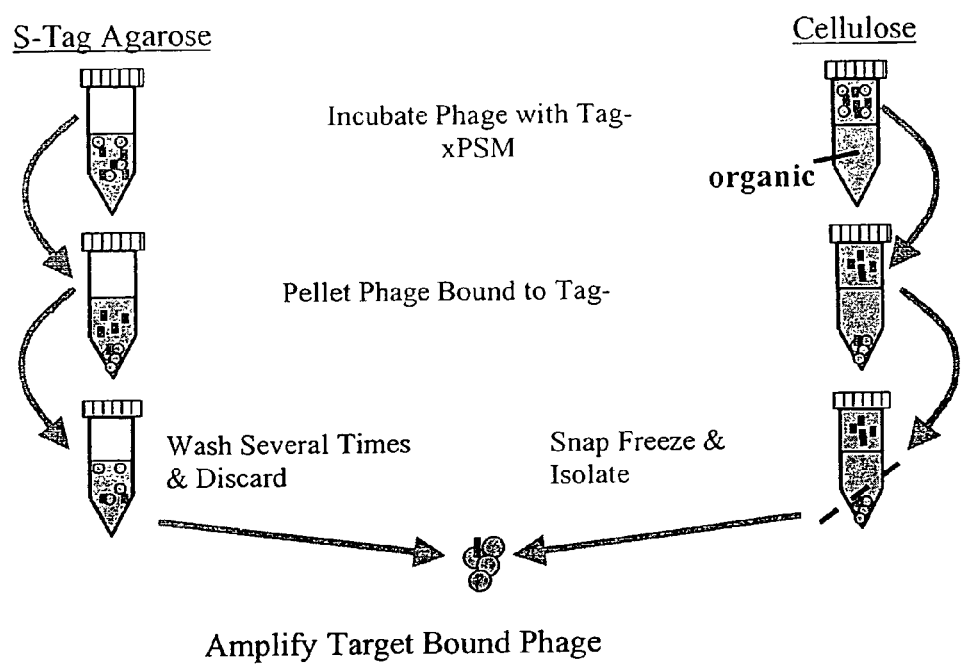
FIG. 2 depicts a schematic of the strategy used for Tag-xPSM phage display.
Figure 3:
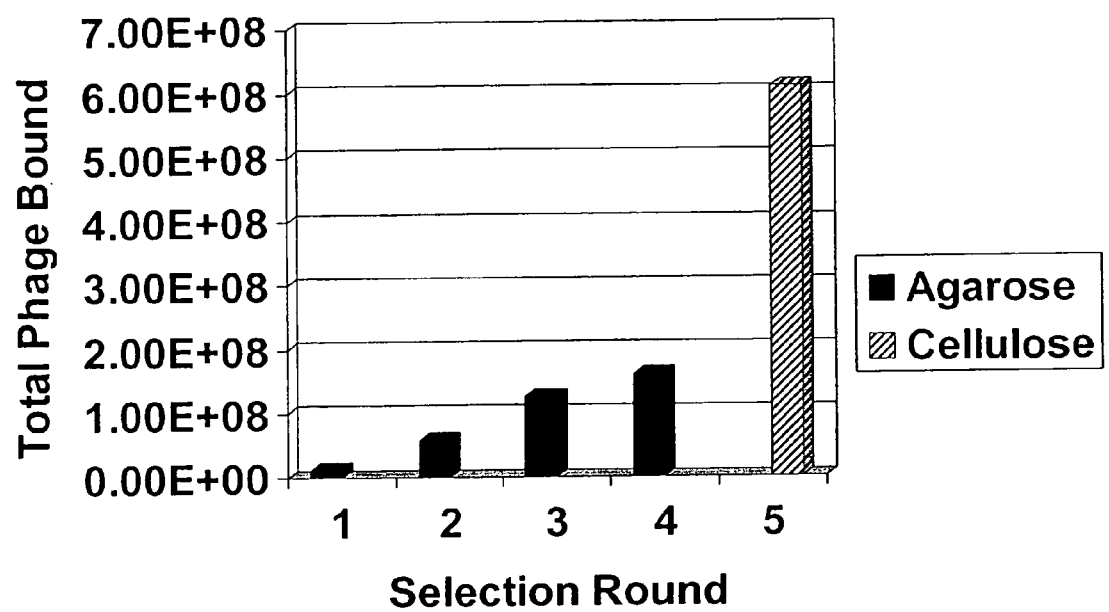
FIG. 3 depicts the quantitation of bound phage during selection of PSMA binding peptides by phage display. $2 \times 10^{11}$ (rounds 1-3) or $2 \times 10^{10}$ PFU of phage were incubated with Tag-xPSM protein bound to an agarose (rounds 1-4) or a cellulose (round 5) substrate. After washing and partitioning, bound phage were quantified by serial dilution titer. Each round of selection resulted in an increased in the number of phage bound.

A library of approximately $1.2 \times 10^9$ random sequence disulfide-constrained heptapeptides displayed on the pIII protein of M13 filamentous bacteriophage was obtained commercially for the identification of PSMA binding peptides. $2 \times 10^{11}$ plaque-forming units (PFU) of the library was incubated with each aliquot of resin for one hour at 37° C., while rotating. The S-tag agarose was pelleted and the supernatant saved as the agarose counter-selected pool. The cellulose resin was transferred onto a 9:1 ratio of dibutyl phthalate:cyclohexane and the resin centrifuged through the organic phase. The aqueous supernatant was saved as the cellulose counter-selected pool. Each counter selected pool was then added to tag-xPSM agarose or cellulose resin, respectively, and incubated for one hour at 37° C., while rotating (see FIG. 2). The Tag-xPSM agarose was pelleted, washed, and saved for phage isolation. The Tag-xPSM cellulose was transferred onto a 9:1 ratio of dibutyl phthalate:cyclohexane and the resin centrifuged through the organic phase. The tube was then snap frozen in liquid nitrogen to isolate the resin pellet. The resulting Tag-xPSM agarose and cellulose were then used to infect ER2738 cells. A small aliquot was taken at this time to quantitate the number of phage bound per round of selection (FIG. 3). The remaining xPSM bound phage was then amplified, tittered, and applied to the next round of phage display. There was only one counter-selection round, followed by a total of five positive selection rounds, applying between $10^{10}$ to $10^{11}$ PFU per round.

In addition to the five consecutive phage display rounds on agarose or cellulose, the products of the fourth round of phage display were cross-selected on the opposite background. For example, phage selected on tag-xPSM agarose was now selected on tag-xPSM cellulose and termed "X-cellulose" for an agarose pool cross-selected onto cellulose. These cross selections were performed to avoid selecting phage peptides specific to the agarose beads or cellulose resin.

Multiple individual phage from rounds three, four, and five of Tag-xPSM phage display were isolated, amplified, and sequenced. The results show multiple sequences that are represented in both the agarose and cellulose selection pools, suggesting that these peptides bind PSMA rather than the solid substrates (Table 1a). Three sequences are highly represented and some are in multiple backgrounds and rounds of selection, indicating that they have truly been selected based on PSMA binding abilities. Additional isolated sequences are shown in Table 1b. Clone names, where given, are named by round (R), background (agarose (A) or cellulose (C)), and clone number.

TABLE 1a

Number of times an individual sequence was found in each round of Tab-xPSM Phage Display. Displayed as Agarose/Cellulose. Cross-selected sequences listed as final selection resin with an asterisk.

| Sequence (Clone No.) | SEQ ID NO: | Round 3 (A/C) | Round 4 (A/C) | Round 5 (A/C) |
|---|---|---|---|---|
| CQKHHNYLC (R5-XC1) | 1 | 0/0 | 0/0 | 0/12* |
| CTITSKRTC (R5-C6) | 2 | 0/1 | 3/3 | 0/3 |
| CTLVPHTRC (R4-C9) | 3 | 0/0 | 13/13 | 0/2 |
| CSHNDTRHC (R5-C3) | 4 | 0/0 | 0/0 | 0/1 |
| CSTRAPHLC (R5-C7) | 5 | 0/0 | 0/0 | 0/1 |
| CHTKHASHC (R5-C8) | 6 | 0/0 | 0/0 | 0/1 |
| CSSHSTVHC (R5-C9) | 7 | 0/0 | 0/0 | 0/1 |
| CKPSMMSYC (R5-C10) | 8 | 0/0 | 0/0 | 0/1 |

TABLE 1a-continued

Number of times an individual sequence was found in each round of Tab-xPSM Phage Display. Displayed as Agarose/Cellulose. Cross-selected sequences listed as final selection resin with an astersisk.

| Sequence (Clone No.) | SEQ ID NO: | Round 3 (A/C) | Round 4 (A/C) | Round 5 (A/C) |
|---|---|---|---|---|
| CPSVNTKQC (R5-C11) | 9 | 0/0 | 0/0 | 0/1 |
| CQTPYDLRC (R5-C2) | 10 | 0/0 | 0/0 | 0/1 |
| CAPNKYKHC (R4-A2) | 11 | 0/0 | 1/0 | 0/0 |
| CTPLSPRYC (R4-C16) | 12 | 0/0 | 0/1 | 0/0 |
| CNKSSLGTC | 13 | 0/0 | 0/1 | 0/0 |
| CHTSLKTHC (R4-C3) | 14 | 0/0 | 0/1 | 0/0 |
| CLKSHSHQC (R4-C6) | 15 | 0/0 | 0/1 | 0/0 |
| CGLPTRTAC (R4-C8) | 16 | 0/0 | 0/1 | 0/0 |
| CHKFQSKMC (R4-C10) | 17 | 0/0 | 0/1 | 0/0 |
| CKHSVSPSC (R4-C1) | 18 | 0/0 | 0/1 | 0/0 |
| CKPTNQHKC (R4-C17) | 19 | 0/0 | 0/1 | 0/0 |
| CDAVRYPVC (R4-C18) | 20 | 0/0 | 0/1 | 0/0 |
| CLSTTISYC (R4-C4) | 21 | 0/0 | 0/1 | 0/0 |
| CTNSNMHHC (R3-A7) | 22 | 1/0 | 0/0 | 0/0 |
| CQFRHSAQC (R3-A5) | 23 | 1/0 | 0/0 | 0/0 |
| CFPQSSDRC | 24 | 1/0 | 0/0 | 0/0 |
| CHTTTDVYC (R3-A12) | 25 | 1/0 | 0/0 | 0/0 |
| CPIMLSEPC | 26 | 1/0 | 0/0 | 0/0 |
| CTSNNSAIC | 27 | 0/1 | 0/0 | 0/0 |
| CLSSNSSLC (R3-C1) | 28 | 0/1 | 0/0 | 0/0 |

TABLE 1b

Additional Sequences

| Sequence (Clone No.) | SEQ ID NO: |
|---|---|
| CQRHDYPAC (R3-A9) | 94 |
| CFPQSSARC (R3-A4) | 95 |
| CPPDRSANC (R3-A6) | 96 |
| CPIPGLRQC (R3-C5) | 97 |
| CPIMLSERC (R3-A1) | 98 |
| CKPNSQPWC (R3-C8) | 99 |
| CKLQHSSTC (R3-A2) | 100 |
| CHRLHSTSC (R3-C2) | 101 |
| CNKTTHYAC (R3-A3) | 102 |
| CTSNNSRIC (R3-C12) | 103 |
| CSSTNSKLC (R3-A10) | 104 |
| CLTSSVNFC (R3-C10) | 105 |
| CQVRHSAQC | 106 |
| CTPQSSDRC | 107 |

The culmination of sequences from multiple rounds and backgrounds also demonstrate similar amino acid composition and charge ratios. There is a clear consensus requirement of two to three adjacent basic amino acid residues, such as lysine, histidine, and arginine. These basic amino acids are also spread between several small non-polar amino acids, such as serine or threonine. Finally, cysteine was commonly followed by glutamine.

Specifically, when all sequences from rounds 3-5 were aligned, three consensus sequences were produced. The alignments are shown in FIGS. 9A-9C.

Example 2

Selection of PSMA Binding Peptides Using LNCaP Cells and xPSM

To ensure that peptides selected to bind Tag-xPSM recognize the native protein on the cell surface, a second selection strategy was developed which utilized the PSMA expressing prostate cancer cell line LNCaP. The results of the second round of Tag-xPSM phage display, from both agarose and cellulose scaffolds, were applied to three consecutive rounds of LNCaP phage display using the Biopanning and Rapid Analysis of Selective Interactive Ligands (BRASIL) technique (Giordano, R. J. et al. (2001) *Nat. Med.* 7:1249-1253). Round two of tag-xPSM phage display was chosen to avoid using an over-selected population that lacked enough diversity to develop new PSMA consensus sequences.

LNCaP and PC-3 monolayers were harvested in phosphate buffered saline (PBS) lacking magnesium and calcium and suspended in suspended in RPMI 1640+1% BSA at a concentration of $10^6$ cells per milliliter. $2\times10^{11}$ PFU from round two of Tag-xPSM agarose and cellulose selections were first incubated with PC-3 cells for two hours on ice, following BRASIL partitioning (centrifugation through 9:1 dibutyl phthalate:cyclohexane and cells centrifuged through the organic phase). The aqueous supernatant was saved as the counter-selected pools. Both counter selected pools were then incubated with LNCaP cells on ice for four hours, mixing occasionally. The cells were then partitioned by the BRASIL technique and the microfuge tube snap-frozen in liquid nitrogen to isolate the cell pellet. The resulting Tag-xPSM agarose and cellulose were then used to infect ER2738 cells. A small aliquot was taken at this time to quantitate the number of phage bound per round of selection. The remaining xPSM bound phage were then amplified, tittered, and applied to the next round of phage display. There was only one counter-selection round, followed by a total of three LNCaP positive selection rounds.

In addition to phage library partitioning by cell binding, a final round of binding was completed on xPSM (Tag-xPSM digested with enterokinase) bound to plastic microtiter plates. This final round was used to ensure that those peptides identified in the LNCaP screen were targeting PSMA and not another unknown surface protein.

Multiple individual phage from rounds three of LNCaP binding and the final round of xPSM binding were isolated, amplified, and sequenced. The results show multiple sequences that are represented in both the LNCaP and xPSM selection pools, suggesting that these peptides bind PSMA rather than the solid substrates (Table 2). Two sequences are highly represented and are found in both cell and purified protein backgrounds.

TABLE 2

Number of times individual sequences were found in LNCaP and xPSM Phage Display

| Sequence | SEQ ID NO: | Round 3 LNCaP | Round 1 xPSM |
|---|---|---|---|
| CTYNPSRWC | 29 | 8 | 7 |
| CLAAPTGKC | 30 | 7 | 12 |
| CNKAALGTC | 31 | 2 | 1 |
| CGSAARNWC | 32 | 1 | 0 |
| CERNTYRFC | 33 | 1 | 0 |
| CKSGEVNYC | 34 | 1 | 0 |
| CTNPNMHHC | 35 | 1 | 0 |
| CPQPASRQC | 36 | 0 | 1 |

These sequences also show a similar requirement for one or two adjacent basic amino acid residues. In addition, a consensus with two adjacent alanines is seen in almost half of the 42 sequences. The sequence CNKAALGTC (SEQ ID NO:31) was also seen in round four of Tag-xPSM cellulose phage display, meaning this sequence was separately selected in both purified PSMA and PSMA expressing cell targets.

Example 3

Individual Phage Bind xPSM and LNCaP Cells

Figure 4:
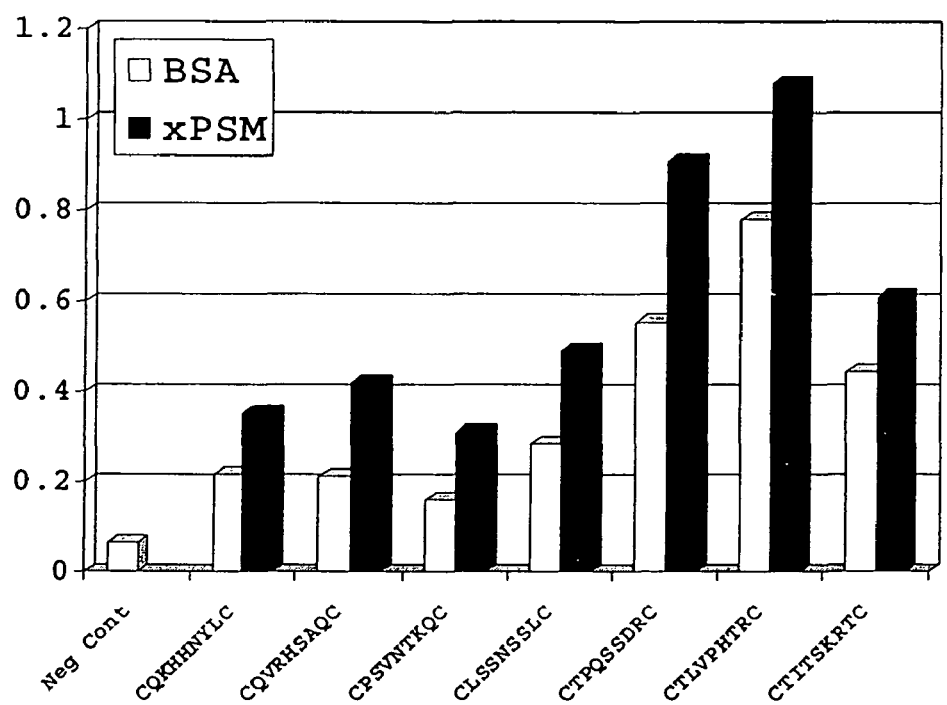
FIG. 4 depicts the binding of individual Tag-xPSM phage to xPSM by ELISA. Peptide sequences of the phage are, in order from left to right, SEQ ID NO:1, SEQ ID NO:106, SEQ ID NO:9, SEQ ID NO:28, SEQ ID NO:107, SEQ ID NO:3, and SEQ ID NO:2.
Figure 5:
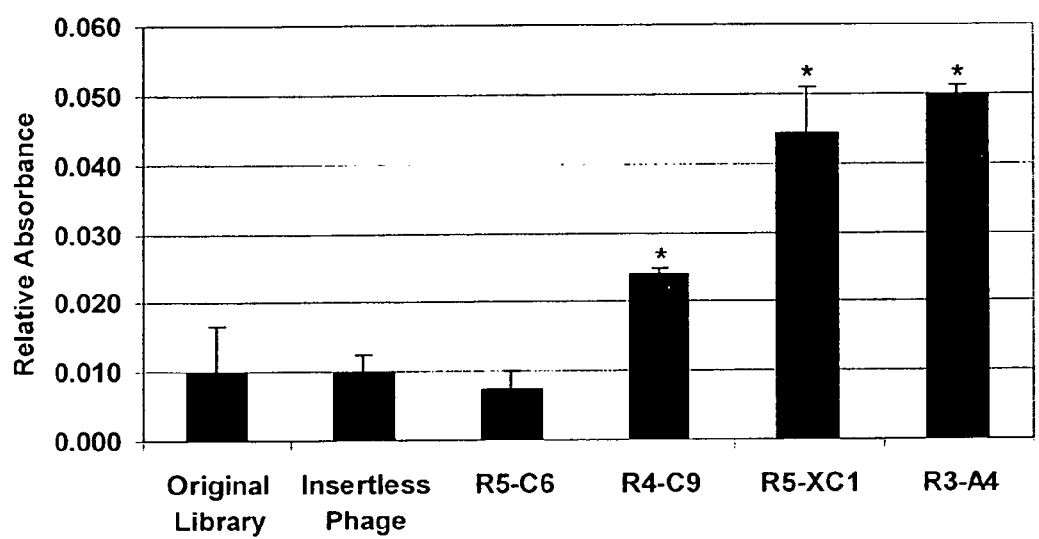
FIG. 5 depicts the binding of selected phage clones to purified extracellular PSMA. Tag-xPSM was immobilized on microtiter plates and targeted for binding with $10^{10}$ PFU of each individual phage. Bound phages were quantified by ELISA absorbance at 410 nm. R4-C9, R5-XC1, and R3-A4 bound with the following significance compared to insertless phage: p-value=0.005, 0.009, and 0.0001 respectively). Phage clones contained peptide sequences as follows: R5-C6: SEQ ID NO:2; R4-C9: SEQ ID NO:5; R5-XC1: SEQ ID NO:1; R3-A4: SEQ ID NO:95.
Figure 6:
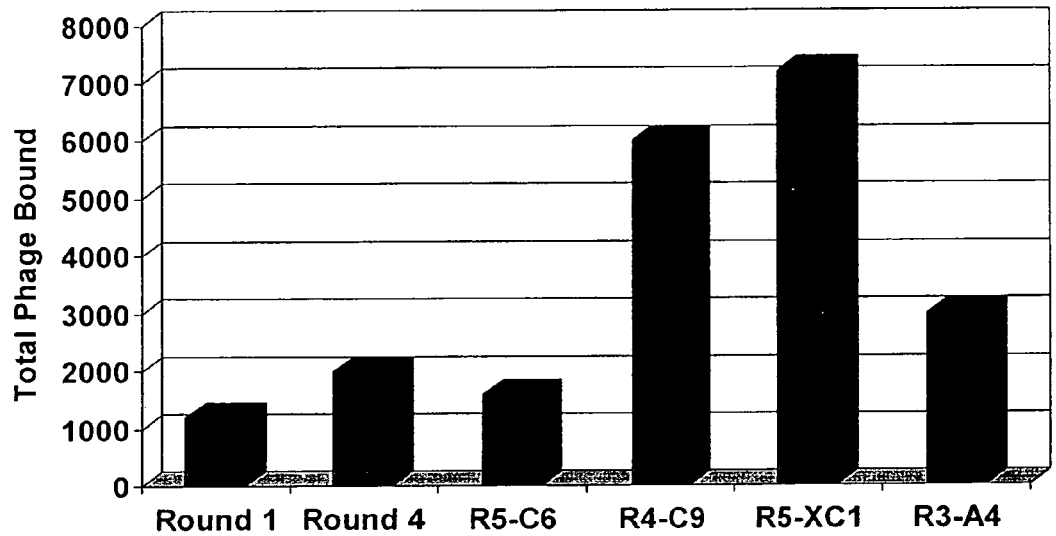
FIG. 6 depicts the binding of individual phage clones to PSMA expressing LNCaP cells. $1.3 \times 10^5$ harvested LNCaP cells were incubated with $10^8$ PFU of each individual phage for 20 minutes. Cell-bound phage were isolated by BRASIL partitioning and titered. Phage clones contained peptide sequences as follows: R5-C6: SEQ ID NO:2; R4-C9: SEQ ID NO:5; R5-XC1: SEQ ID NO:1; R3-A4: SEQ ID NO:95.
Figure 7:
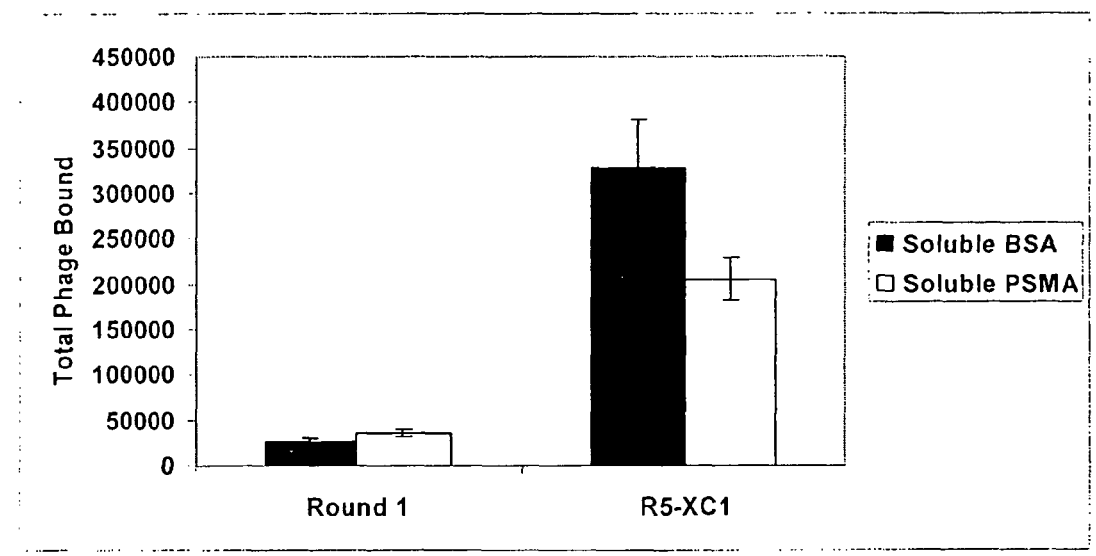
FIG. 7 depicts the specific blocking of LNCaP phage binding by soluble xPSM protein. $10^{10}$ R5-XC1 phage or the round one phage pool were allowed to bind LNCaP cells in the presence of 380 nM PSMA or 500 nM BSA. PSMA significantly block R5-XC1 phage binding (p=0.014). R5-XC1 (containing the peptide of SEQ ID NO: 1) bound LNCaP significantly better than the round one phage pool in the presence of PSMA or BSA (p=0.000001 and 0.000013, respectively).

Each Tag-xPSM selected phage was individually tested for the ability to bind to xPSM and LNCaP cells. The results show that each phage more tightly binds xPSM by ELISA (FIGS. 4 and 5) than controls. Each phage bound the PSMA expressing cell line LNCaP tighter than phage from early selection rounds (FIG. 6). The phage selection shows improved affinity for LNCaP with four rounds of selection. Further, soluble xPSM was capable of blocking one phage from binding LNCaP cells (FIG. 7). These data, as well as the selection and sequencing data, suggest that we have successfully identified peptides that bind to the extracellular portion of PSMA.

Figure 8:
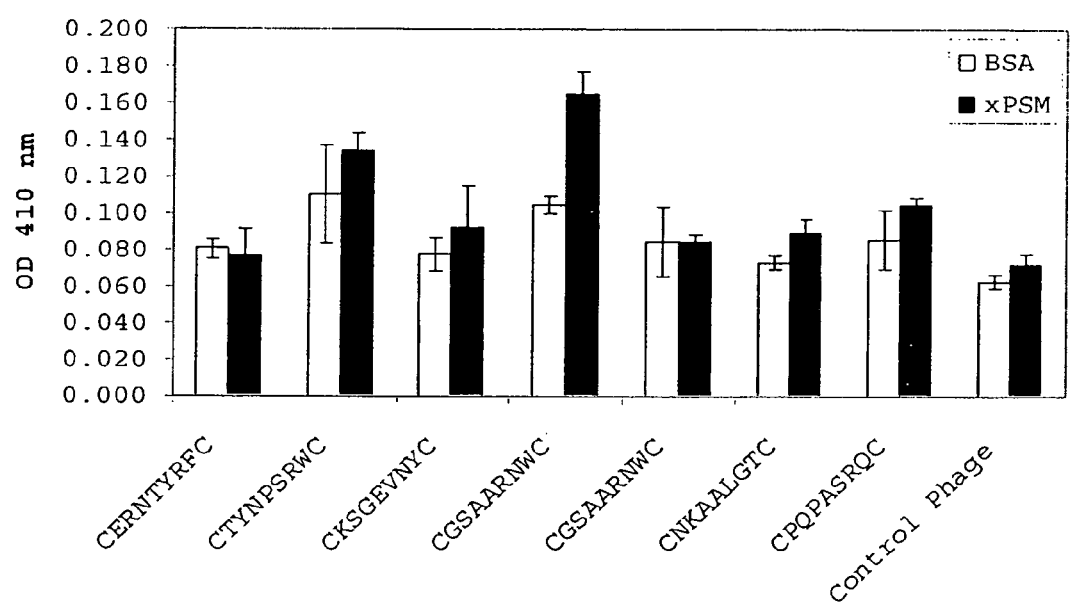
FIG. 8 depicts binding of individual phage to xPSM by ELISA. Peptide sequences of the phage are, in order from left to right, SEQ ID NO:33, SEQ ID NO:29, SEQ ID NO:34, SEQ ID NO:32, SEQ ID NO:32, SEQ ID NO:31, and SEQ ID NO:36.

Further testing of LNCaP selected phage confirmed the ability for some of these to bind xPSM (FIG. 8).

Example 4

Selection of PSMA Binding Peptides Using Tag-xPSM Under Higher Stringency Binding Conditions This example describes the screening of the original library, consisting of approximately $1.2\times10^9$ random sequence heptapeptides displayed on the pill protein of M13 filamentous bacteriophage, for peptides that bind to the PSMA fusion protein Tag-xPSM, under more stringent conditions in order to identify higher affinity peptides.

As described above in Example 1, Tag-xPSM was used as a target for the in vitro selection of a commercially available cysteine-constrained heptapeptide phage library. For the initial round, 14 micrograms of S-protein-agarose immobilized Tag-xPSM was incubated with $2\times10^{11}$ PFU for 30 minutes at room temperature while rotating. Weakly bound phage were then washed off with three 5 minute rotating washes. One phage pool, referred to herein as the "pH 2.2 pool", was eluted for ten minutes in pH 2.2 glycine buffer followed by neutralization in Tris buffer. Those phage still bound to Tag-xPSM were then eluted for one hour in 30 mM EDTA-Tris buffer. This pool is referred to herein as the "EDTA pool". These two pools where then carried separately for the next three rounds. Stringency was increased in each round by changing Tag-xPSM substrate background, decreasing binding time, or increasing washing time (Table 3).

TABLE 3

Conditions for the stringent selection of PSMA binding peptides by phage display.

| Round | Conditions |
|---|---|
| 1 | 14 µg Tag-xPSM Agarose<br>0.1% BSA with 30 minute pre-block<br>30 minute binding<br>3 × 5 minute TBST washes |
| 2 | 17 µg Tag-xPSM Cellulose<br>0.1% BSA with 30 minute pre-block<br>30 minute binding<br>3 × 5 minute TBST washes |

TABLE 3-continued

Conditions for the stringent selection of PSMA binding peptides by phage display.

| Round | Conditions |
|---|---|
| 3 | 7 µg Tag-xPSM Agarose<br>0.1% BSA with 30 minute pre-block<br>10 minute binding<br>3 × 30 minute TBST washes |
| 4 | 10 µg Tag-xPSM Cellulose<br>0.1% BSA with 30 minute pre-block<br>10 minute binding<br>3 × 30 minute TBST washes |

The enhanced affinity of each round was determined by comparing the number of phage bound to Tag-xPSM substrate versus substrate without fusion protein. As the rounds continued, the signal to noise grew to over 200 by round 4 (FIG. 7).

Twelve individual phage from each elution condition for rounds two, three, and four of Tag-xPSM phage display were isolated, amplified, and sequenced. All clones sequenced from rounds 2 and 3 were unique (Tables 4 and 5).

TABLE 4

Sequences of stringent round 2 phages clones

| Clone | SEQ ID NO: | Sequence |
|---|---|---|
| Rnd2 pH 2.2-G2 | 37 | CVSPNLHDC |
| Rnd2 pH 2.2-G3 | 38 | CNALQWKEC |
| Rnd2 pH 2.2-G4 | 39 | CNTQPPRTC |
| Rnd2 pH 2.2-G5 | 40 | CLDQNYFYC |
| Rnd2 pH 2.2-G6 | 41 | CNLLYSRTC |
| Rnd2 pH 2.2-G7 | 42 | CPAPENKNLC |
| Rnd2 pH 2.2-G8 | 43 | CPKGMFNSC |
| Rnd2 pH 2.2-G9 | 44 | CLGMKMRAC |
| Rnd2 pH 2.2-G10 | 45 | CSTNWQLSC |
| Rnd2 pH 2.2-G11 | 46 | CSEWTWNNC |
| Rnd2 pH 2.2-G12 | 47 | CKPQRLTTC |
| Rnd2 pH EDTA-E1 | 48 | CNAKLSLQC |
| Rnd2 pH EDTA-E2 | 49 | CLSAINRVC |
| Rnd2 pH EDTA-E3 | 50 | CSLHTSTTC |
| Rnd2 pH EDTA-E5 | 51 | CTPDGTLTC |
| Rnd2 pH EDTA-E6 | 52 | CQPNLRPMC |
| Rnd2 pH EDTA-E7 | 53 | CHPPKSLYC |
| Rnd2 pH EDTA-E8 | 54 | CTQAHRLIC |
| Rnd2 pH EDTA-E9 | 55 | CPKTMYLGC |
| Rnd2 pH EDTA-E10 | 56 | CSTLIHLMC |
| Rnd2 pH EDTA-E11 | 57 | CDLHLRSEC |
| Rnd2 pH EDTA-E12 | 58 | CTPENTHQC |

TABLE 5

Sequences of stringent round 3 phages clones

| Clone | SEQ ID NO: | Sequence |
|---|---|---|
| Rnd3 pH 2.2-G1 | 59 | CPPNRLQMC |
| Rnd3 pH 2.2-G2 | 60 | CLNTAPLAC |
| Rnd3 pH 2.2-G3 | 61 | CKLRTQMAC |
| Rnd3 pH 2.2-G4 | 62 | CLNPHFSNC |
| Rnd3 pH 2.2-G5 | 63 | CSSYSLQVC |
| Rnd3 pH 2.2-G6 | 64 | CGHSTSKTC |
| Rnd3 pH 2.2-G7 | 65 | CAPKLRFNC |
| Rnd3 pH 2.2-G8 | 66 | CVHPHGNQC |
| Rnd3 pH 2.2-G9 | 67 | CMGLNTGRC |
| Rnd3 pH 2.2-G10 | 68 | CSNVKVWNC |
| Rnd3 pH 2.2-G11 | 69 | CTAAFPAFC |
| Rnd3 pH 2.2-G12 | 70 | CHRWPPYAC |
| Rnd3 pH EDTA-E1 | 71 | CLRITMQTC |
| Rnd3 pH EDTA-E2 | 72 | CPETGRQSC |
| Rnd3 pH EDTA-E3 | 73 | CTSRYDDQC |
| Rnd3 pH EDTA-E4 | 74 | CPPWAAPYC |
| Rnd3 pH EDTA-E5 | 75 | CPMSSPSYC |
| Rnd3 pH EDTA-E6 | 76 | CSRLYSAAC |
| Rnd3 pH EDTA-E7 | 77 | CTKGLLPRC |
| Rnd3 pH EDTA-E8 | 78 | CLMVKPPSC |
| Rnd3 pH EDTA-E9 | 79 | CLTEASRLC |
| Rnd3 pH EDTA-E10 | 80 | CLQNPCATC |
| Rnd3 pH EDTA-E11 | 81 | CKQTSANEC |
| Rnd3 pH EDTA-E12 | 82 | CNTPLIKVC |

By round 4, a few peptide sequences had taken over each pool (Table 6). The acid elution round was 83% one sequence, CLNTAPLAC (SEQ ID NO:60), which was present as a single clone in round 3. Two consensus sequences were identified in the EDTA elution pool, CSLNTRSQC (SEQ ID NO:85) and CSTHRAWPC (SEQ ID NO:86).

TABLE 6

Sequences of stringent round 4 phages clones

| Clone | SEQ ID NO: | Sequence |
|---|---|---|
| Rnd4 pH 2.2-G1 | 60 | CLNTAPLAC |
| Rnd4 pH 2.2-G2 | 60 | CLNTAPLAC |
| Rnd4 pH 2.2-G3 | 60 | CLNTAPLAC |
| Rnd4 pH 2.2-G4 | 60 | CLNTAPLAC |
| Rnd4 pH 2.2-G5 | 60 | CLNTAPLAC |

TABLE 6-continued

Sequences of stringent round 4 phages clones

| Clone | SEQ ID NO: | Sequence |
|---|---|---|
| Rnd4 pH 2.2-G6 | 60 | CLNTAPLAC |
| Rnd4 pH 2.2-G7 | 60 | CLNTAPLAC |
| Rnd4 pH 2.2-G10 | 66 | CVHPHGNQC |
| Rnd4 pH 2.2-G11 | 60 | CLNTAPLAC |
| Rnd4 pH 2.2-G12 | 60 | CLNTAPLAC |
| Rnd4 pH 2.2-G8 | 83 | CSPVGPAFC |
| Rnd4 pH 2.2-G9 | 84 | CRTTSDALC |
| Rnd4 pH EDTA-E1 | 85 | CSLNTRSQC |
| Rnd4 pH EDTA-E10 | 85 | CSLNTRSQC |
| Rnd4 pH EDTA-E4 | 86 | CSTHRAWPC |
| Rnd4 pH EDTA-E5 | 86 | CSTHRAWPC |
| Rnd4 pH EDTA-E2 | 87 | CSEALNPIC |
| Rnd4 pH EDTA-E6 | 88 | CQSLLAKKC |
| Rnd4 pH EDTA-E7 | 89 | CHFHHTGAC |
| Rnd4 pH EDTA-E8 | 90 | CNPASHQLC |
| Rnd4 pH EDTA-E9 | 91 | CPSTLGMTC |
| Rnd4 pH EDTA-E11 | 92 | CWHYPANNC |
| Rnd4 pH EDTA-E12 | 93 | CNSYHTHHC |

Example 5

Peptide Synthesis

Peptide compounds of the invention can be prepared by solid-phase peptide synthesis using an N-α-9-fluorenylmethyloxycarbonyl (FMOC)-based protection strategy as follows. Starting with 2.5 mmoles of FMOC-Val-Wang resin, sequential additions of each amino acid are performed using a four-fold excess of protected amino acids, 1-hydroxybenzotriazole (HOBt) and diisopropyl carbodiimide (DIC). Recouplings are performed when necessary as determined by ninhydrin testing of the resin after coupling. Each synthesis cycle is minimally described by a three minute deprotection (25% piperidine/N-methyl-pyrrolidone (NMP)), a 15 minute deprotection, five one minute NMP washes, a 60 minute coupling cycle, five NMP washes and a ninhydrin test. The peptide is removed from the resin by treatment with trifluoroacetic acid (TFA) (82.5%), water (5%), thioanisole (5%), phenol (5%), ethanedithiol (2.5%) for two hours followed by precipitation of the peptide in cold ether. The solid is pelleted by centrifugation (2400 rpm.times.10 min.), and the ether decanted. The solid is resuspended in ether, pelleted and decanted a second time. The solid is dissolved in 10% acetic acid and lyophilized to dryness.

Alternatively, peptide compounds of the invention can be prepared on an Advanced ChemTech Model 396 multiple peptide synthesizer using an automated protocol established by the manufacturer for 0.025 mmole scale synthesis. Double couplings are performed on all cycles using 2-(1H-benzotriazol-1-yl)-1,1,3,3-tetramethyluronium hexafluorophosphate (HBTU)/N,N-diisopropylethylamine (DIEA)/HOBt/FMOC-AA in four-fold excess for 30 minutes followed by DIC/HOBt/FMOC-AA in four-fold excess for 45 minutes. The peptide is deprotected and removed from the resin by treatment with TFA/water (95%/5%) for three hours and precipitated with ether as described above. The pellet is resuspended in 10% acetic acid and lyophilized. The material is purified by a preparative HPLC using 15%-40% acetonitrile over 80 minutes on a Vydac C18 column (21×250 mm).

Example 6

Enhancement of PMSA Enzymatic Activity by PMSA Binding Peptides

Enzyme assays often provide a sensitive means to analyze protein-protein interactions. The enzymatic activity of PSMA has been well studied and previously used to demonstrate protein-ligand interactions with high sensitivity (Lupold, S. E. et al. (2002) *Cancer Res.* 62(14):4029-33).

N-acetyl-aspartyl-glutamate (NAAG) hydrolysis was performed essentially as previously described (Robinson, M. B. et al. (1987) *J. Biol. Chem.* 262:14498-506, incorporated herein by reference). In short, 65 ng purified xPSM was resuspended in NAALADase Buffer (50 mM Tris, pH 7.4, 0.5% Triton X-100) and incubated in the presence of peptides or inhibitors (1, 10, and 100 micromolar), along with the radiolabeled substrate N-acetyl-L-aspartyl-L-[3,4-$^3$H] glutamate (NEN Life Science Products, Boston, Mass.) at 30 nM. Reactions were run at 37° C. for 10 minutes. The reaction was then stopped by the addition of an equal volume of ice-cold 100 mM sodium phosphate, 2 mM EDTA. Products were separated from intact substrate using AG 1-X8 Formate resin (BioRad Laboratories, Hercules, Calif.) anion exchange chromatography. The reaction product, tritiated-glutamate, was eluted with 1M sodium formate and quantitated by scintillation counting. Intact NAAG remained in the column resin. Experiments were completed in triplicate and have been repeated. The data represents six data points from two experiments. Experiments were designed to allow 20% or less of the total substrate to be cleaved.

Figure 10:
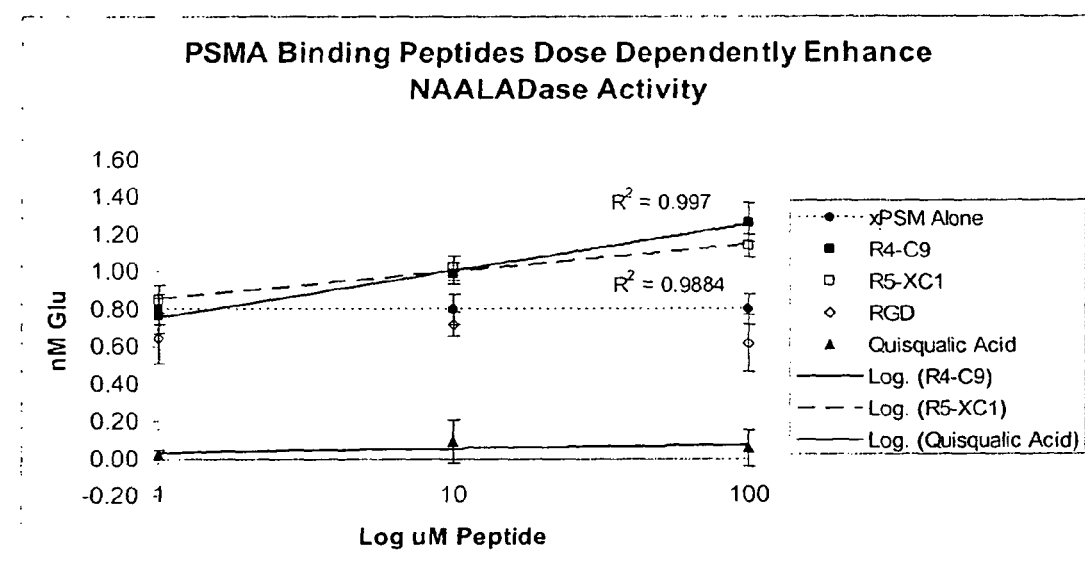
FIG. 10 depicts the dose-dependent enhancement of NAALADase activity by PSMA binding peptides.
Figure 11:
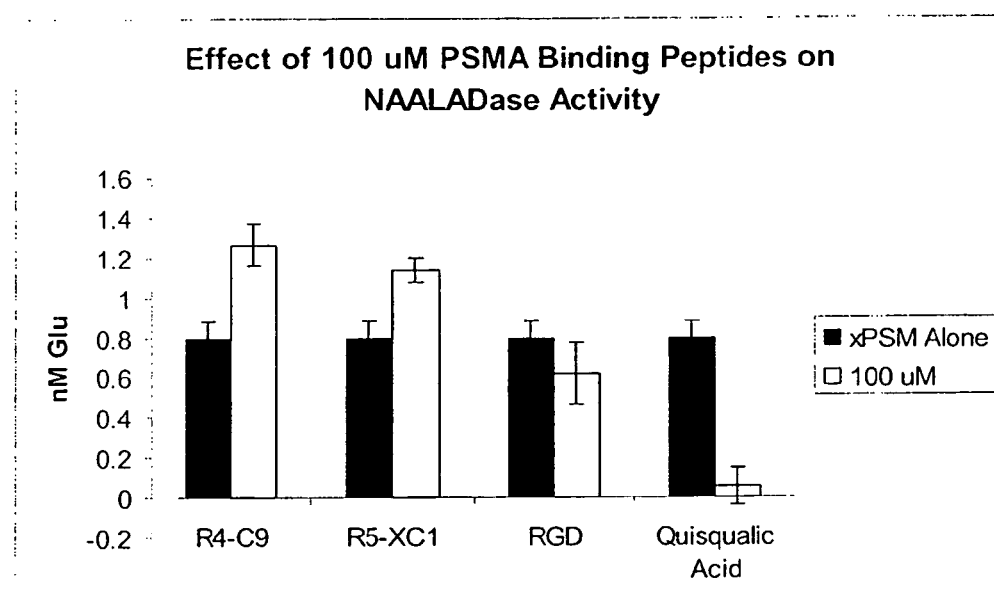
FIG. 11 depicts the effect of 100 µM PSMA binding peptides on NAALADase activity.

PSMA enzymatic activity was inhibited, as expected, by the potent NAALADase inhibitor quisqualic acid. However, two selected PSMA binding peptides enhanced, rather than inhibited, enzyme activity in a dose dependant manner (FIGS. 10 and 11). This data suggests that peptides bind and stabilize PSMA, leading to enhanced enzymatic activity. Peptide enhancement is significant with p-values of 0.0001 (100 uM R5-XC1), 0.0001 (100 uM R4-C9), 0.015 (10 uM R5-XC1), and 0.024 (10 uM R4-C9).

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A peptide compound which selectively binds to the extracellular portion of human PSMA and comprises the amino acid sequence QKHHNYL (SEQ ID NO:109).

2. The peptide of claim 1, wherein the peptide consists of the amino acid sequence QKHHNYL (SEQ ID NO:109).

3. The peptide of claim 1, wherein the peptide comprises a cysteine residue at the N and C terminus.

4. The peptide of claim 3, wherein the peptide is cyclic.

5. A peptide which selectively binds to the extracellular portion of human PSMA, wherein the peptide comprises the amino acid sequence set forth as SEQ ID NO:1.

6. A peptide which selectively binds to the extracellular portion of human PSMA and comprises the amino acid sequence QKHHNYL (SEQ ID NO:109), and wherein the peptide is 9 amino acid residues in length.

7. The peptide of claim 5 or 1, wherein the peptide is 9 amino acid residues in length.

* * * * *